United States Patent
Rossi et al.

(10) Patent No.: US 9,464,293 B2
(45) Date of Patent: Oct. 11, 2016

(54) RNA APTAMERS FOR THERAPEUTIC AND DIAGNOSTIC DELIVERY TO PANCREATIC CANCER CELLS

(71) Applicant: CITY OF HOPE, Duarte, CA (US)

(72) Inventors: John J. Rossi, Azusa, CA (US); Sorah Yoon, Pasadena, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

(21) Appl. No.: 14/391,997

(22) PCT Filed: Mar. 13, 2013

(86) PCT No.: PCT/US2013/031074
§ 371 (c)(1),
(2) Date: Oct. 10, 2014

(87) PCT Pub. No.: WO2013/154735
PCT Pub. Date: Oct. 17, 2013

(65) Prior Publication Data
US 2015/0197752 A1 Jul. 16, 2015

Related U.S. Application Data

(60) Provisional application No. 61/622,375, filed on Apr. 10, 2012.

(51) Int. Cl.
| | |
|---|---|
| *C12N 15/11* | (2006.01) |
| *A61K 48/00* | (2006.01) |
| *C07H 21/04* | (2006.01) |
| *C12N 15/115* | (2010.01) |
| *C07H 21/02* | (2006.01) |
| *A61K 31/7105* | (2006.01) |
| *A61K 31/7088* | (2006.01) |
| *A61K 47/48* | (2006.01) |

(52) U.S. Cl.
CPC .......... *C12N 15/115* (2013.01); *A61K 31/7088* (2013.01); *A61K 31/7105* (2013.01); *A61K 47/48092* (2013.01); *C07H 21/02* (2013.01); *C12N 15/111* (2013.01); *C12N 2310/16* (2013.01); *C12N 2310/351* (2013.01); *C12N 2320/32* (2013.01)

(58) Field of Classification Search
CPC . C12N 15/115; C12N 2310/16; C12N 15/113
See application file for complete search history.

(56) References Cited

U.S. PATENT DOCUMENTS

| | | | |
|---|---|---|---|
| 7,524,630 B2 | 4/2009 | Tan et al. | |
| 7,655,785 B1 * | 2/2010 | Bentwich | 536/24.1 |
| 2009/0286854 A1 | 11/2009 | Missailidis et al. | |
| 2010/0254901 A1 | 10/2010 | Smith | |
| 2011/0052697 A1 | 3/2011 | Farokhzad et al. | |
| 2012/0142013 A1 * | 6/2012 | Lee et al. | 435/6.14 |

FOREIGN PATENT DOCUMENTS

| | | |
|---|---|---|
| WO | 9965928 | 12/1999 |
| WO | WO 2004036190 A2 * | 4/2004 |
| WO | WO 2007128109 A1 * | 11/2007 |

OTHER PUBLICATIONS

Alderson, D., et al., "Guidelines for the Management of Patients with Pancreatic Cancer Periampullary and Ampullary Carcinomas," Gut 54(Suppl. V): v1-v16 (2005).
Alexakis, N., et al., "Current Standards of Surgery for Pancreatic Cancer," Br. J. Surg. 91:1410-1427 (2004).
Blank, M., et al., "Systematic Evolution of a DNA Aptamer Binding to Rat Brain Tumor Microvessels," J. Biol. Chem. 276(19):16464-16468 (2001).
Cunningham, D., et al., "Phase III Randomized Comparison of Gemcitabine Versus Gemcitabine Plus Capecitabine in Patients With Advanced Pancreatic Cancer," J. Clin. Oncol. 27(33):5513-5518 (2009).
Daniels, D. A., et al., "A Tenascin-C Aptamer Identified by Tumor Cell SELEX: Systematic Evolution of Ligands by Exponential Enrichment," PNAS 100(26)15416-15421 (2003).
Ellington, A. D., et al., "In Vitro Selection of RNA Molecules that Bind Specific Ligands," Nature 346:818-822 (1990).
Esposito, C. L, et al., "A Neutralizing RNA Aptamer Against EGFR Causes Selective Apoptotic Cell Death," PLoS One 6(9):e24071 (2011).
Fulda, S., "Apoptosis Pathways and Their Therapeutic Exploitation in Pancreatic Cancer," J. Cell. Mol. Med. 13 (7):1221-1227 (2009).
Ghaneh, P., et al., "Recent Advances in Clinical Practice: Biology and Management of Pancreatic Cancer," Gut 56:1134-1152 (2007).
Heinemann, V., et al., Cancer Treatment Reviews 38:843-853 (2012).
Hicke, B. J., et al., "Tenascin-C Aptamers are Generated Using Tumor Cells and Purified Protein," J. Biol. Chem. 276(52):48644-48654 (2001).

(Continued)

*Primary Examiner* — Dana Shin
(74) *Attorney, Agent, or Firm* — Perkins Coie LLP; Lara Dueppen

(57) ABSTRACT

In some embodiments, aptamers that specifically bind pancreatic cancer cells are provided. Such aptamers may include an RNA molecule that specifically binds a pancreatic cancer cell surface protein. In certain embodiments, the RNA molecule that is used as an aptamer may include a nucleotide sequence of GAAUGCCC (SEQ ID NO: 8). In other embodiments, the RNA molecule may include a nucleotide sequence of SEQ ID NO:1, SEQ ID NO:2, SEQ ID NO:3, SEQ ID NO:4, SEQ ID NO:5, or SEQ ID NO:6. In certain embodiments, the aptamer may be conjugated to one or more therapeutic agents (e.g., an shRNA molecule, an siRNA molecule, an mRNA molecule, or an miRNA molecule), one or more diagnostic agents, or a combination thereof. The aptamers and their conjugates may be used to deliver therapeutic agents to a pancreatic cancer cell, and/or in methods for treating or diagnosing pancreatic cancer.

15 Claims, 19 Drawing Sheets
(17 of 19 Drawing Sheet(s) Filed in Color)

(56) References Cited

OTHER PUBLICATIONS

Hwang, B., et al., "hnRNP L is Required for the Translation Mediated by HCV IRES," Biochem. Biophys. Res. Commun. 378:584-588 (2009).

Jemal, A., et al., "Cancer Statistics, 2009," CA Cancer J. Clin. 59:225-249 (2009).

Klinkenbijl, J. H., et al., "Adjuvant Radiotherapy and 5-Fluorouracil After Curative Resection of Cancer of the Pancreas and Periampullary Region Phase III Trial of the EORTC Gastrointestinal Tract Cancer Cooperative Group," Annals of Surgery 230(6):776-784 (1999).

Neoptolemos, J. P., et al., "A Randomized Trial of Chemoradiotherapy and Chemotherapy After Resection of Pancreatic Cancer," New Eng. J. Med. 350:1200-1210 (2004).

Oettle, H., et al., "Adjuvant Chemotherapy with Gemcitabine vs Observation in Patients Undergoing Curative-Intent Resection of Pancreatic Cancer," JAMA 297:267-277 (2007).

"Pancreatic Cancer in the UK," Lancet 378:1050 (2011).

Rhim, A. D., et al., "EMT and Dissemination Precede Pancreatic Tumor Formation," Cell 148(1-2):349-361 (2012).

Rivera, F., et al., "Treatment of Advanced Pancreatic Cancer: From Gencitabine Single Agent to Combinations and Targeted Therapy," Cancer Treatment Reviews 35:335-339 (2009).

Saif, M. W., et al., "Adjuvant Treatment of Pancreatic Cancer in 2009: Where Are We? Highlights from the '45th ASCO Annual Meeting'. Orlando, FL, USA. May 29-Jun. 2, 2009," J. Pancreas. (Online) 10(4):373-377 (2009).

Schneider, G., et al., "Pancreatic Cancer: Basic and Clinical Aspects," Gastroenterology 128:1606-1625 (2005).

Sebolt-Leopold, J., et al., "Mechanisms of Drug Inhibition of Signalling Molecules," Nature 441:457-462 (2006).

Stathis, A., et al., "Advanced Pancreatic Carcinoma: Current Treatment and Future Challenges," J. Nat. Rev. Clin. Oncol. 7:163-172 (2010).

Tuerk, C., "Using the SELEX Combinatorial Chemistry Process to Find High Affinity Nucleic Acid Ligands to Target Molecules," Methods in Molecular Biology 67:219-230 (1997).

Ulrich, H., et al., "In Vitro Selection of RNA Aptamers that Bind to Cell Adhesion Receptors of Trypanosoma Cruzi and Inhibit Cell Invasion," J. Biol. Chem. 277(23):20756-20762 (2002).

Vincent, A., et al., "Pancreatic Cancer," Lancet 363(9414):1049-1057 (2004).

United States Patent and Trademark Office, International Search Report and Written Opinion for PCT/US13/31074 dated Sep. 9, 2013.

Wang, J., et al., "In Vitro Selection of Novel RNA Ligands that Bind Human Cytomegalovirus and Block Viral Infection," RNA 6:571-583 (2000).

Wilson, D. S., et al., "In Vitro Selection of Functional Nucleic Acids," Annu. Rev. Biochem. 68:611-647 (1999).

Wong, H. H., et al., "Pancreatic Cancer: Molecular Pathogenesis and New Therapeutic Targets," Nat. Rev. Gastroenterol. Hepatol. 6(7):412-422 (2009).

Zhou, J., et al., "Novel Dual Inhibitory Function Aptamer-siRNA Delivery System for HIV-1 Therapy," Mol. Ther. 16 (8):1481-1489 (2008).

Zhou, J., et al., "The Therapeutic Potential of Cell-Internalizing Aptamers," Current Topics in Medicinal Chemistry 9:1144-1157 (2009).

Zuker, M., "Mfold Web Server for Nucleic Acid Folding and Hybridization Prediction," Nucleic Acids Res. 31(13):3406-3415 (2003).

Cerchia, L., et al., "Targeting Cancer Cells with Nucleic Acid Aptamers," Trends in Biotechnology 28:517-525 (2010).

Cibiel, A., et al., "Methods to Identify Aptamers Against Cell Surface Biomarkers," Pharmaceuticals 4:1216-1235 (2011).

European Patent Office, Extended European Search Report dated Feb. 1, 2016 for European Application No. 13775956.9.

Kanwar, J. R., et al., "Chimeric Aptamers in Cancer Cell-Targeted Drug Delivery," Critical Reviews in Biochemistry and Molecular Biology 46(6):459-477 (2011).

Keefe, A. D., et al., "Selex with Modified Nucleotides," Current Opinion in Chemical Biology 12:448-456 (2008).

Kim, Y.H., et al., "An RNA Aptamer that Specifically Binds Pancreatic Adenocarcinoma Up-Regulated Factor Inhibits Migration and Growth of Pancreatic Cancer Cells," Cancer Letters 313:76-83 (2011).

Rialon, K. L., et al., "Aptamers: Potential Applications to Pancreatic Cancer Therapy," Anti-Cancer Agents in Medicinal Chemistry 11:434-441 (2011).

Sun, W., et al., "Advances and Perspectives in Cell-Specific Aptamers," Current Pharmaceutical Design 17:80-91 (2011).

Ulrich, H., et al., "Disease-Specific Biomarker Discovery by Aptamers," Cytometry Part A 75A:727-733 (2009).

Ye, M., et al., "Generating Aptamers by Cell-SELEX for Applications in Molecular Medicine," Int. J. Mol. Sci. 13:3341-3353 (2012).

\* cited by examiner

Figure 5A-B
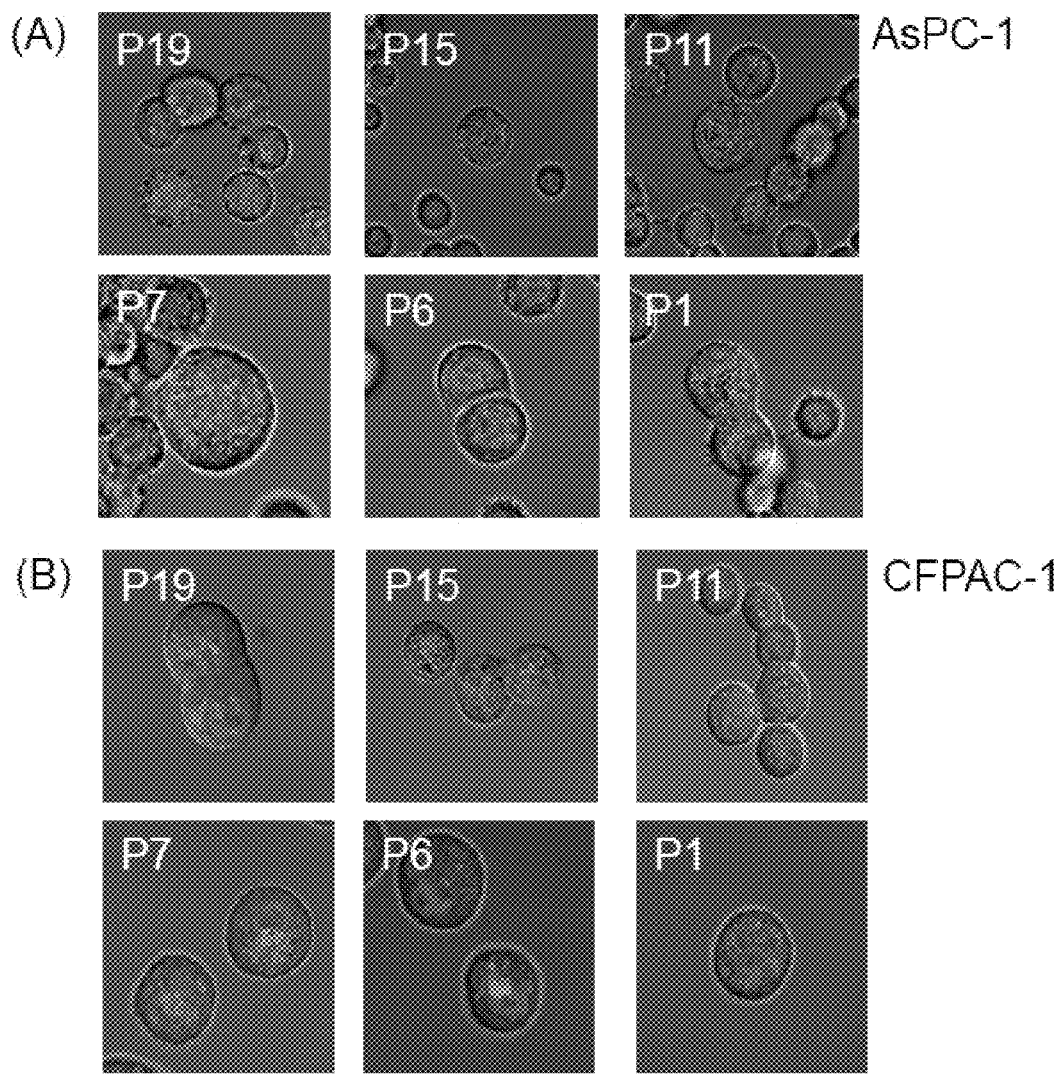

Figure 5C-D
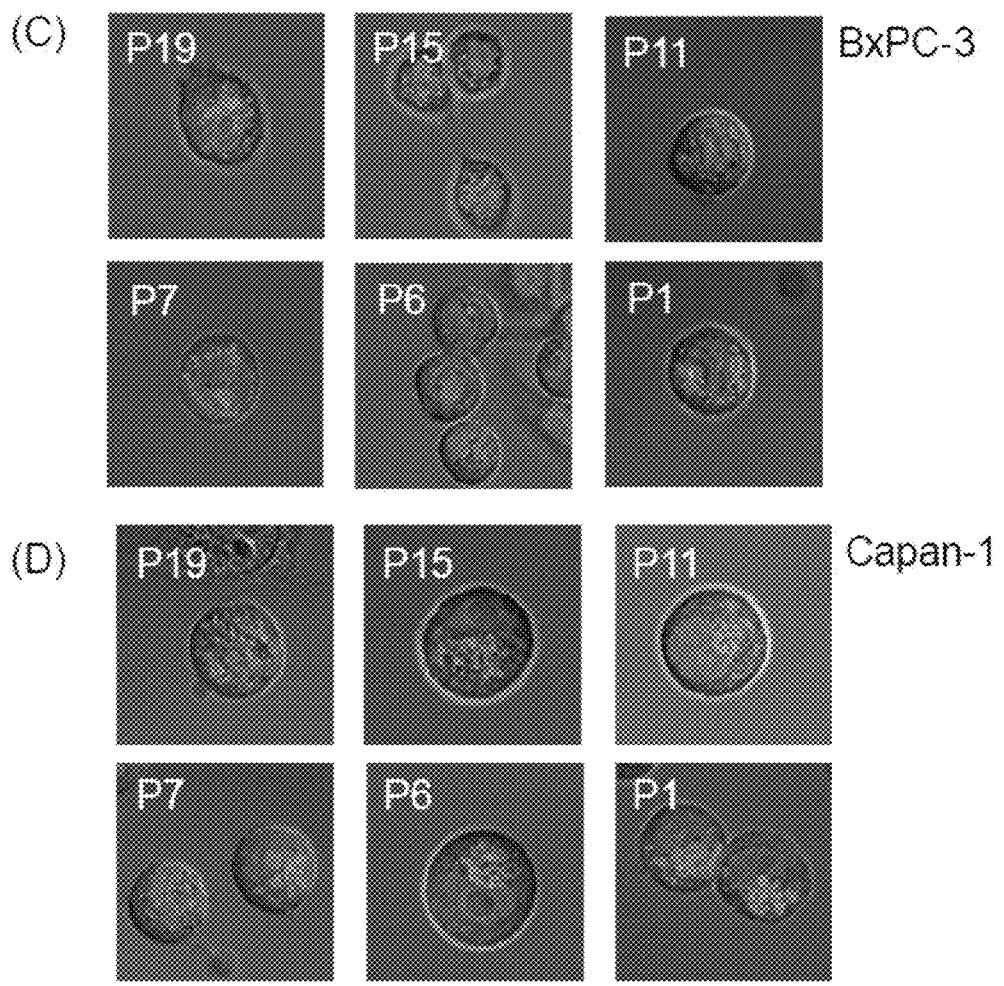

Tumor engraftment for 2 weeks in SCID mice
10ug P1+P19 injection, 4 times injection, measure the cancer volume (mm^3)
* TTEST: P value <0.05

RNA APTAMERS FOR THERAPEUTIC AND DIAGNOSTIC DELIVERY TO PANCREATIC CANCER CELLS

PRIORITY CLAIM

This application claims priority to U.S. Provisional Patent Application No. 61/622,375, filed Apr. 10, 2012, the subject matter of which is hereby incorporated by reference as if fully set forth herein.

BACKGROUND

Pancreatic ductal adenocarcinoma (PDAC) is the fourth most common cause of cancer death in the United States, accounting for 30,000 deaths yearly in the United States (Jemal et al. 2009). Pancreatic cancer is characterized by a rapid disease progression and absence of specific symptoms, largely precluding an early diagnosis and meaningful treatment (Stathis & Moore, 2010; Schneider et al. 2005).

Despite aggressive efforts to improve treatment for patients with pancreatic cancer, limited progress has been made (Stathis & Moore 2010; Pancreatic Cancer UK 2011). Although improvement is being made through the development of improved targeted and systemic therapies, the prognosis and treatment of pancreatic cancer is still inadequate. This is due both to the late presentation and the lack of an effective treatment strategy (Li et al. 2004). As a result, gemcitabine as a single agent given postoperatively remains the current standard of care. Combinations with other chemotherapeutic drugs or biological agents given as a palliative setting for unresectable pancreatic cancer or adjuvant setting following resection have resulted in limited improvement (Klinkenbijl et al. 1999; Neoptolemus et al. 2004; Oettle et al. 2007). The 5 yr survival of patients with pancreatic cancer, despite numerous phase 3 trials, remains less than 5% after resection (Vincent et al. 2011; Alexakis 2004; Ghaneh 2007, BSG 2005). The majority of patients will present with either local or systemic recurrence within 2 years following resection and postoperative adjuvant chemotherapy (Vincent et al. 2011; Alexakis 2004; Ghaneh 2007). Currently, the most effective single agent gemcitabine achieves an improved 1-year survival rate from 16 to 19%. Treatment with conventional treatments such as gemcitabine or 5-flurouracil (5-FU) results in a median survival of just a few months (Saif 2009; Rivera et al. 2009). The addition of Tarceva® (erlotinib) in a randomized study added a median of 11 days to overall survival (Cunningham 2009; Heinemann 2012).

This limitation of conventional treatment is due to the profound resistance of PDAC cells towards anti-cancer drugs emerging from the efficient protection against chemotherapeutic drugs (Wong & Lemoine 2009; Fulda 2009). Therefore, it is important to develop new therapeutic strategies for this devastating disease.

SUMMARY

In some embodiments, aptamers that specifically bind pancreatic cancer cells are provided. Such pancreatic cancer cell aptamers may include an RNA molecule that specifically binds a pancreatic cancer cell surface protein. The RNA molecule that is used as an aptamer in accordance with the embodiments described herein may include a nucleotide sequence of GAAUGCCC (SEQ ID NO: 8). In certain embodiments, the RNA molecule may include a nucleotide sequence of SEQ ID NO:1, SEQ ID NO:2, SEQ ID NO:3, SEQ ID NO:4, SEQ ID NO:5, or SEQ ID NO:6. In certain embodiments, the aptamer may be conjugated to one or more therapeutic agents, one or more diagnostic agents, or a combination thereof. In some aspects the one or more therapeutic agents may be selected from an shRNA molecule, an siRNA molecule, an mRNA molecule, or an miRNA molecule.

In some embodiments, methods for delivering a therapeutic agent to a pancreatic cancer cell are provided. Such methods may include a step of contacting the pancreatic cancer cell with a pancreatic cancer cell aptamer conjugate. The pancreatic cancer cell aptamer conjugate may include a pancreatic cell aptamer component and a therapeutic agent component. In some aspects the pancreatic cell aptamer component includes an RNA molecule that specifically binds a pancreatic cancer cell surface protein, resulting in internalization of the pancreatic cell aptamer conjugate—such as those described herein. The therapeutic agent component may include any suitable therapeutic agent that can be conjugated to an mRNA molecule including, but not limited to, an shRNA molecule, an siRNA molecule, an mRNA molecule, or an miRNA molecule.

In other embodiments, methods for treating pancreatic cancer are provided. Such a method may include a step of administering a therapeutically effective amount of a pancreatic cell aptamer, wherein the pancreatic cell aptamer comprises an RNA molecule that specifically binds a pancreatic cancer cell surface protein, and wherein the pancreatic cell aptamer prevents binding of a pancreatic cell ligand. The RNA molecule that is used as an aptamer in accordance with the embodiments described herein may include a nucleotide sequence of GAAUGCCC (SEQ ID NO: 8). In certain embodiments, the RNA molecule may include a nucleotide sequence of SEQ ID NO:1, SEQ ID NO:2, SEQ ID NO:3, SEQ ID NO:4, SEQ ID NO:5, or SEQ ID NO:6. In certain embodiments, the aptamer may be conjugated to one or more therapeutic agents, one or more diagnostic agents, or a combination thereof. In some embodiments, the aptamers may be part of a pharmaceutical composition for use in the methods of treating pancreatic cancer. Said pharmaceutical compositions may further comprise one or more additional therapeutic agents (e.g., chemotherapeutics).

BRIEF DESCRIPTION OF THE DRAWINGS

This application contains at least one drawing executed in color. Copies of this application with color drawing(s) will be provided by the Office upon request and payment of the necessary fees.

DETAILED DESCRIPTION

Figure 1:
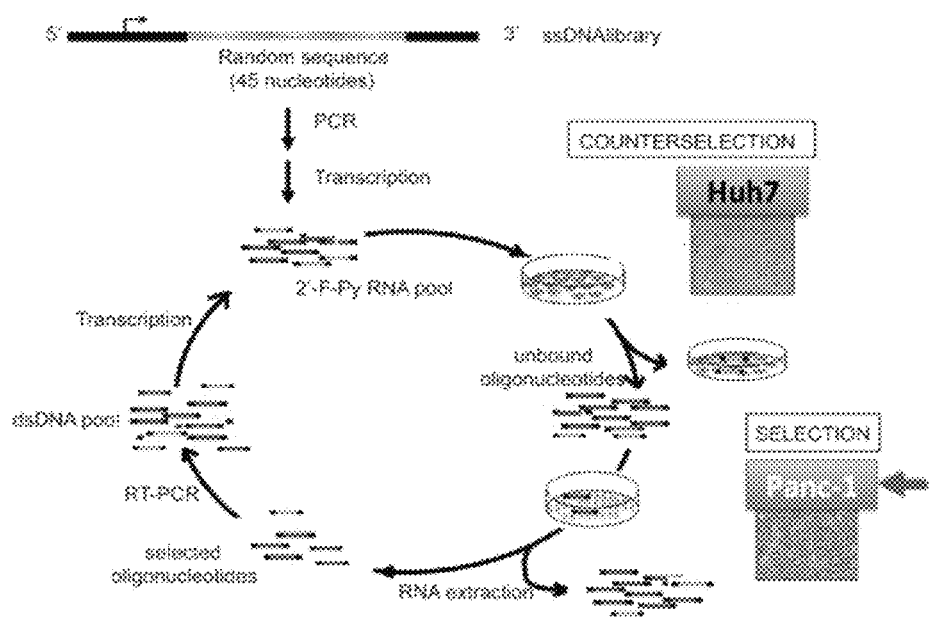
FIG. 1 is a schematic diagram illustrating a selection/counterselection SELEX process for selecting pancreatic cancer cell-specific aptamers according to some embodiments. Briefly, a population of 2'F-Py RNAs was incubated with a non-pancreatic cancer cell line (Huh7 hepatocarcinoma cell line) or a healthy pancreatic cell line for the counterselection step. Unbound oligonucleotides sequences were recovered and incubated with a pancreatic cancer cell line (Panc-1) for the selection step. Unbound sequences were discarded and bound sequences were recovered by total RNA extraction. Sequences enriched by the selection step are then amplified before the subsequent cycle of selection. (SELEX method based on an adapted version of Esposito et al. 2011).
Figure 2A:
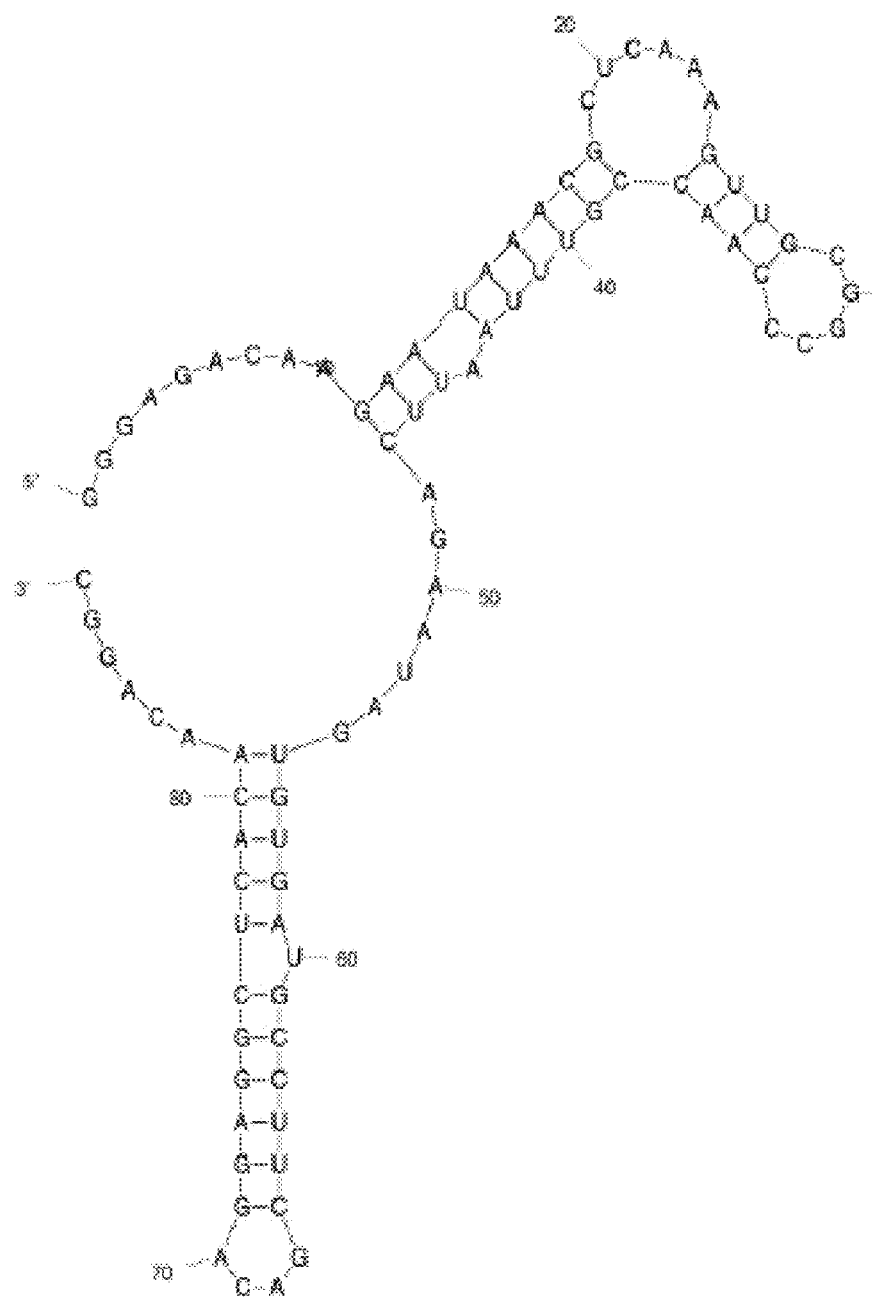
FIG. 2 shows the secondary structure of six RNA aptamers selected from randomized N40 RNA libraries according to some embodiments. The secondary structures of the six aptamers, (A) SEQ ID NO:1; (B) SEQ ID NO:2; (C) SEQ ID NO:3; (D) SEQ ID NO:4; (E) SEQ ID NO:5; and (F) SEQ ID NO:6; were predicted using the Mfold program.
Figure 2B:
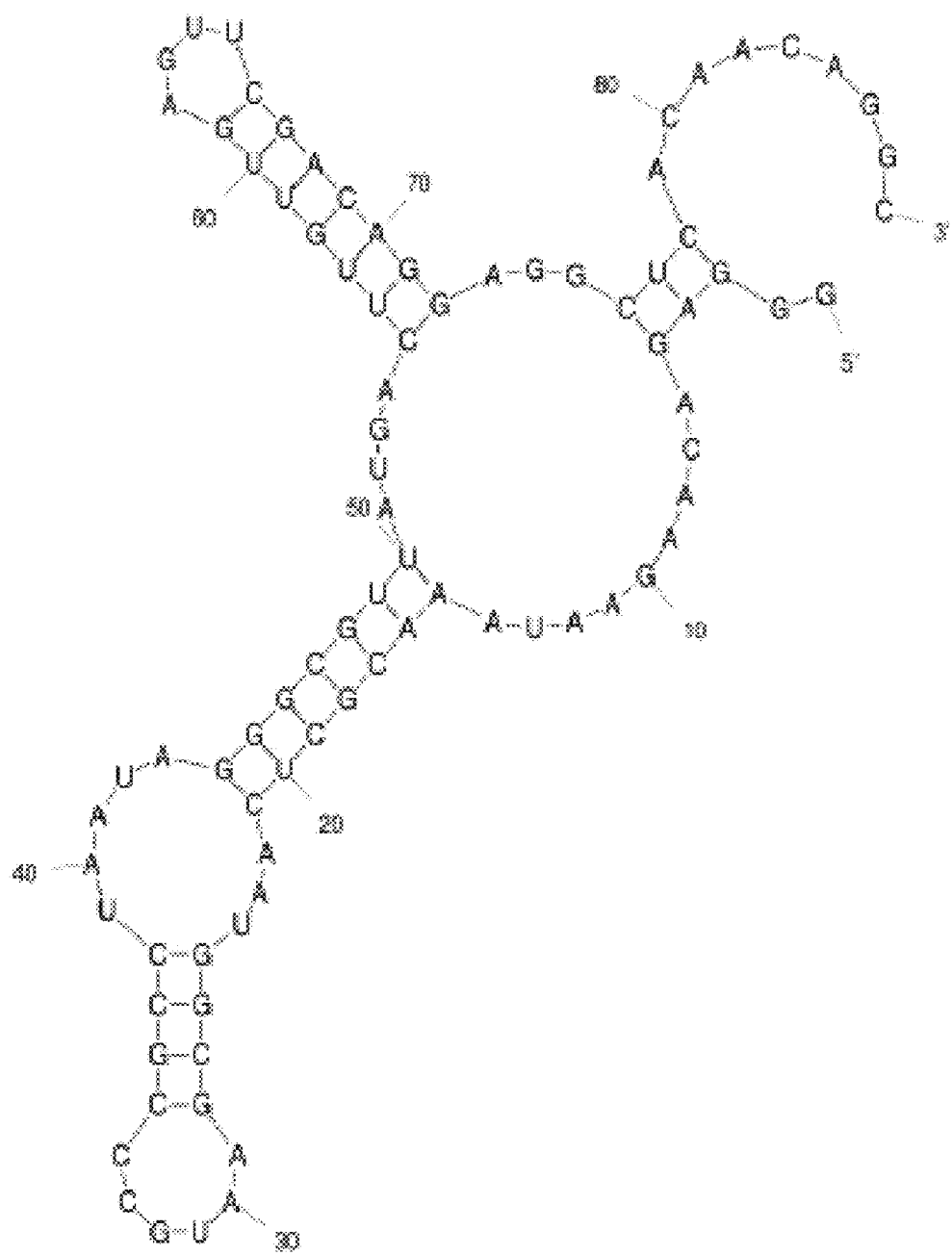
Figure 2C:
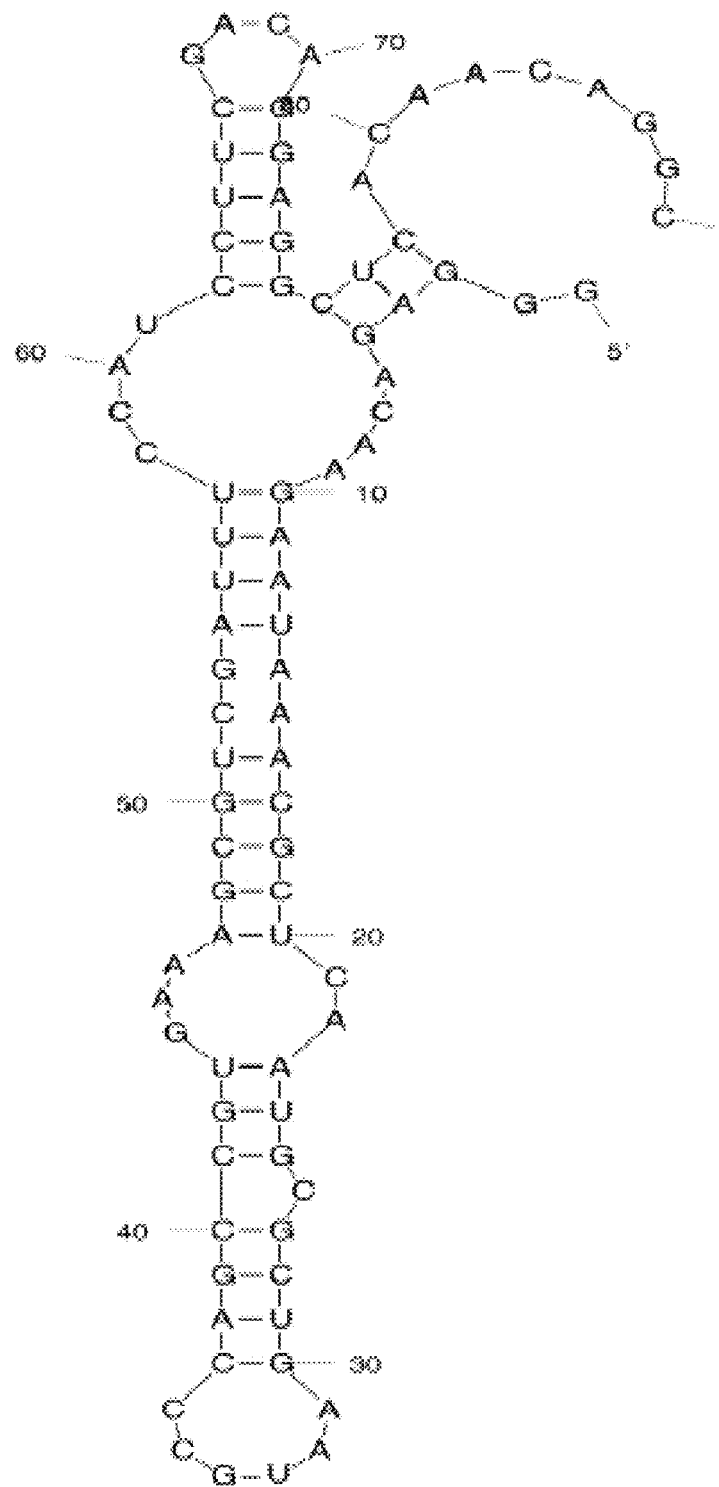
Figure 2D:
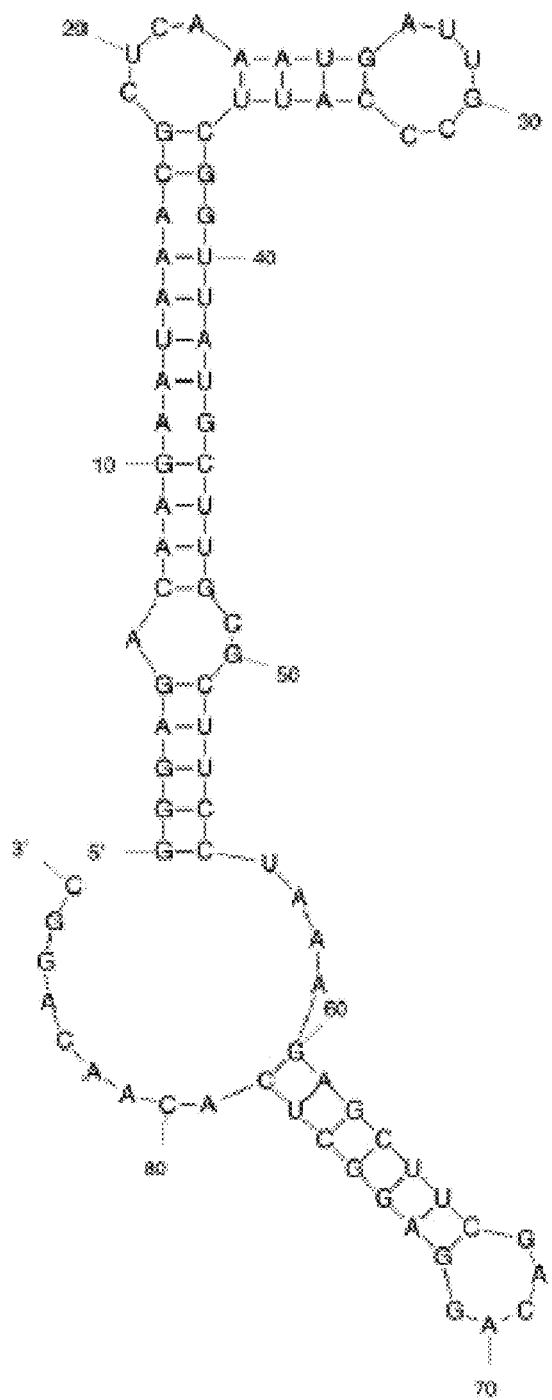
Figure 2E:
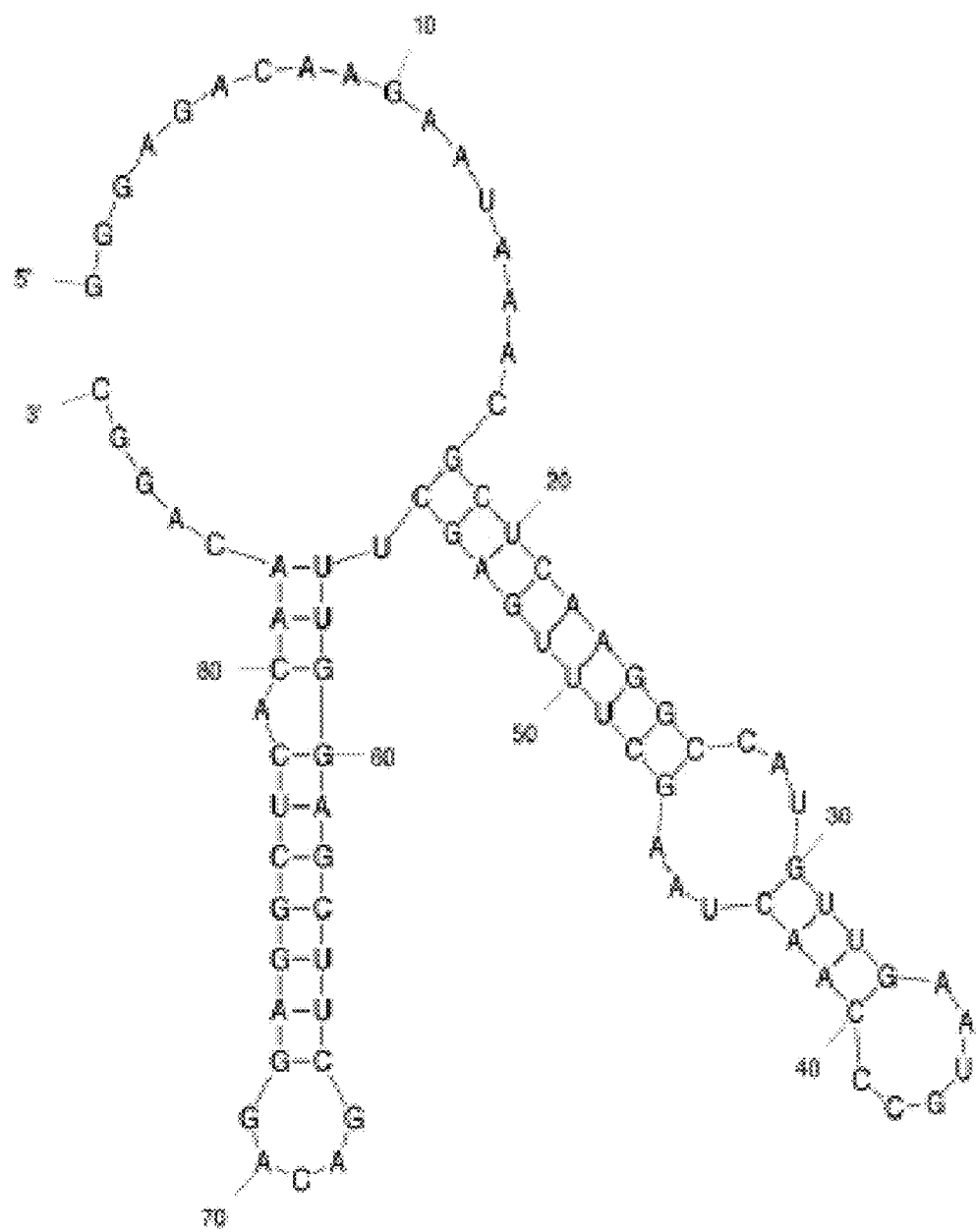
Figure 2F:
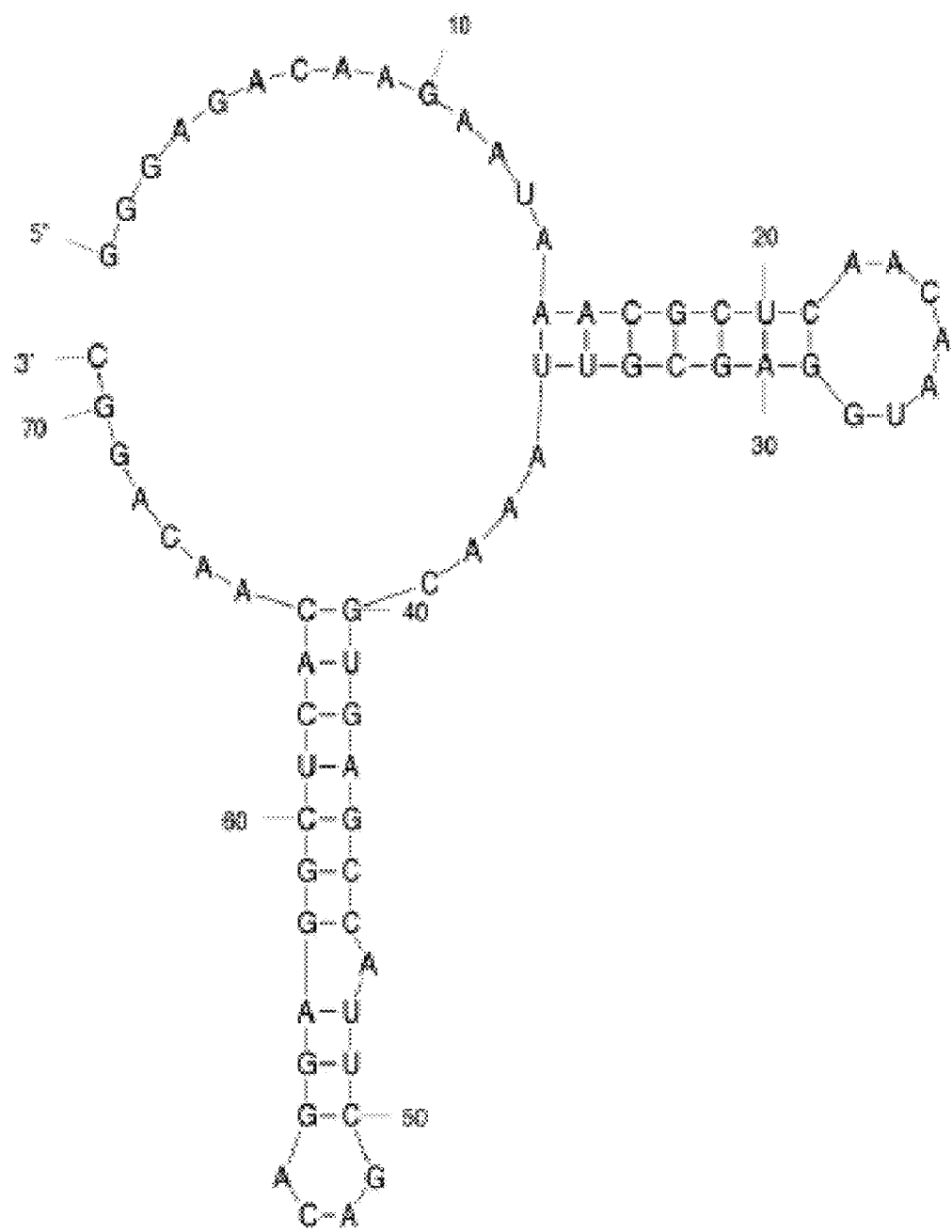

Pancreatic cancer cell aptamers, systems for cell specific delivery and methods for their use are provided herein. According to the embodiments described herein, the pancreatic cancer cell aptamers may be used alone or in combination with therapeutic or diagnostic agents and molecules for treatment, diagnosis and monitoring of pancreatic cancer.

Aptamers

In one embodiment, aptamers for targeting pancreatic cancer cells are provided. Said aptamers may be used for treating pancreatic cell cancer, malignancies or for any other disease or condition related to pancreatic cells. An "aptamer" is any suitable small molecule, such as a nucleic acid or a peptide molecule that binds specifically to a target, such as a small molecule, protein, nucleic acid, cell, tissue or organism. Aptamers that target specific cell surface proteins can be employed as delivery molecules to target a distinct cell type, thereby reducing off-target effects or other unwanted side effects. Further, by binding a specific cell surface protein, the aptamers may also be used as a therapeutic agent on their own.

In some embodiments, the aptamer (or aptamer component) is a nucleic acid aptamer. Such aptamers with binding affinities in nanomolar range have been utilized for flexible applications ranging from diagnostic to therapeutic assay formats (Zhou & Rossi 2009). Moreover, aptamers that target specific cell surface proteins may be employed as delivery molecules to target a distinct cell type, hence reducing off-target effects or other unwanted side effects (Zhou et al. 2008). In certain embodiments, the nucleic acid aptamer is an RNA aptamer. An RNA aptamer may be any suitable RNA molecule that can be used on its own as a stand-alone molecule, or may be integrated as part of a larger RNA molecule having multiple functions, such as an RNA interference molecule in accordance with some embodiments. For example, the pancreatic cell aptamer may be located in an exposed region of an shRNA molecule (e.g., the loop region of the shRNA molecule) to allow the shRNA or miRNA molecule to bind a surface receptor on the target cell, then after it is internalized, is processed by the target cell's RNA interference pathways.

The nucleic acid that forms the nucleic acid aptamer may comprise naturally occurring nucleosides, modified nucleosides, naturally occurring nucleosides with hydrocarbon linkers (e.g., an alkylene) or a polyether linker (e.g., a PEG linker) inserted between one or more nucleosides, modified nucleosides with hydrocarbon or PEG linkers inserted between one or more nucleosides, or a combination of thereof. In some embodiments, nucleotides or modified nucleotides of the nucleic acid aptamer can be replaced with a hydrocarbon linker or a polyether linker provided that the binding affinity and selectivity of the nucleic acid aptamer is not substantially reduced by the substitution.

According to the embodiments described herein, aptamers that target and selectively bind pancreatic cancer cells are generated and selected. Selection of aptamers may be accomplished by any suitable method known in the art, including an optimized protocol for in vitro selection, known as SELEX (Systemic Evolution of Ligands by Exponential enrichment). Although the SELEX process has been established as a general technique for aptamer selection, it is not predictable nor is it standardized for use with any target. Instead, the SELEX process must be optimized and customized for each particular target molecule. Each SELEX experiment includes its own challenges and is not guaranteed to work for all targets.

Many factors are important for successful aptamer selection. For example, the target molecule should be stable and easily reproduced for each round of SELEX, because the SELEX process involves multiple rounds of binding, selection, and amplification to enrich the nucleic acid molecules. In addition, the nucleic acids that exhibit specific binding to the target molecule have to be present in the initial library. Thus, it is advantageous to produce a highly diverse nucleic acid pool. Because the starting library is not guaranteed to contain aptamers to the target molecule, the SELEX process for a single target may need to be repeated with different starting libraries. Aptamer selection using SELEX is unpredictable. Even when all of the factors are optimized for successful aptamer selection, the SELEX process does not always yield viable aptamers for every target molecule.

In some embodiments, selection of an aptamer may be accomplished by applying a SELEX process against whole living/intact cells in culture to obtain aptamers that selectively target an antigen that is specifically expressed on a target cell. A whole cell SELEX process may include an approach that includes both counterselection and selection, which is specifically designed for enrichment of aptamers against cell surface tumor-specific targets (FIG. 1). As described in detail in the Examples below, a SELEX process was used to generate a panel of RNA aptamers that are able to bind pancreatic cancer cells, but do not bind unrelated cancer cell or healthy cell types. In certain embodiments, the pancreatic cancer cell aptamers have a sequence that may include SEQ ID NO:1, SEQ ID NO:2, SEQ ID NO:3, SEQ ID NO:4, SEQ ID NO:5, or SEQ ID NO:6, which are described in detail in the Example below and in FIGS. 2A-2F.

As described in the Examples below, at least two aptamers have been determined to be effective in reducing tumor size. These aptamers share a common nucleotide motif GAAUGCCC (SEQ ID NO: 8). As such, a pancreatic cell aptamer used in accordance with the embodiments described herein may include a nucleotide sequence of GAAUGCCC (SEQ ID NO: 8).

The aptamers described herein target a cell surface molecule or an endocytotic membrane associated protein (e.g., a membrane receptor or a glycoprotein) that is overexpressed on pancreatic cancer cells or is specifically expressed only on pancreatic cancer cells. As such, the aptamer selection process described above may be used to develop aptamers that bind known cell surface molecules and endocytotic membrane associated proteins, or may also be used to discover new cell surface molecules that act as pancreatic cell biomarkers and are specific to pancreatic cells.

According to the embodiments described herein, the pancreatic cancer cell aptamers can act as a cell-specific delivery vehicle, a therapeutic agent, or both. Further, these aptamers are likely able to inhibit or suppress proliferation of pancreatic cancer cells or otherwise interfere with a cancerous pathway by blocking a receptor or other membrane associated protein, preventing a ligand from binding. Therefore, the pancreatic cancer cell aptamers may be used for at least two functions: inhibition of proliferation and survival of pancreatic cancer cells and as a delivery vehicle for therapeutic and/or diagnostic agents. As described below, the pancreatic cancer cell aptamers can deliver therapeutic or diagnostic agents efficiently to pancreatic cancer cell lines.

Aptamer Conjugates

According to some embodiments, the aptamers described herein may be conjugated to a therapeutic agent, forming a therapeutic aptamer conjugate. As used herein, the term "conjugated to," or "conjugate" refers to two or more entities or the state of two or more entities which are linked by a direct or indirect covalent or non-covalent interaction. In some embodiments, an association is covalent. In some embodiments, a covalent association is mediated by a linker moiety. In some embodiments, an association is non-covalent (e.g. charge interactions, affinity interactions, metal coordination, physical adsorption, host-guest interactions, hydrophobic interactions, stacking interactions, hydrogen bonding interactions such as with "sticky sequences," van der Waals interactions, magnetic interactions, electrostatic interactions, dipole-dipole interactions, etc.). In this case, the pancreatic cancer cell aptamers described herein may be used as a cell-specific delivery vehicle to deliver a therapeutic or diagnostic payload to pancreatic cancer cells.

According to some embodiments, the pancreatic cancer cell aptamers described herein may be conjugated to one or more therapeutic agents to form a therapeutic aptamer conjugate. A "therapeutic agent" as used herein is an atom, molecule, or compound that is useful in the treatment of cancer or other conditions described herein. Examples of therapeutic agents that may be conjugated to a pancreatic cell aptamer include, but are not limited to, drugs, chemotherapeutic agents, therapeutic antibodies and fragments thereof, toxins, radioisotopes, enzymes (e.g., enzymes to cleave prodrugs to a cytotoxic agent at the site of the tumor), nucleases, hormones, immunomodulators, antisense oligonucleotides, nucleic acid molecules (e.g., mRNA molecules, cDNA molecules or RNAi molecules such as siRNA or shRNA), chelators, boron compounds, photoactive agents and dyes. The therapeutic agent may also include a metal, metal alloy, intermetallic or core-shell nanoparticle bound to a chelator that acts as a radiosensitizer to render the targeted cells more sensitive to radiation therapy as compared to healthy cells. Further, the therapeutic agent may include paramagnetic nanoparticles for MRI contrast agents (e.g., magnetite or $Fe_3O_4$) and may be used with other types of therapies (e.g., photodynamic and hyperthermal therapies) and imaging (e.g., fluorescent imaging (Au and CdSe)).

In certain embodiments, the pancreatic cell aptamer is conjugated to a nucleic acid molecule which acts as the therapeutic agent. In some embodiments, the nucleic acid molecule that is conjugated to the aptamer is an RNA molecule. RNA molecules that may be conjugated to the aptamer in accordance with the embodiments described herein may include, but are not limited to, ribosomal RNA (rRNA), messenger RNA (mRNA), transfer RNA (tRNA), small nuclear RNA (snRNA), small nucleolar RNA (snoRNA), small cytoplasmic RNA (snRNA), micro RNA (miRNA), small interfering RNA (siRNA), and short hairpin RNA (shRNA).

In one aspect, the nucleic acid molecule is an RNA interference molecule (e.g., an siRNA or shRNA molecule) that, when delivered to a target cell by the aptamer, is internalized by the cell and acts to suppress or silence the expression of one or more oncogenes or of any protein or peptide that is associated with cancer by targeting an mRNA molecule. In one embodiment, the RNA interference molecule is (i) an siRNA, shRNA, miRNA or other RNA molecule which targets an mRNA molecule which encodes K-ras (V-Ki-ras2 Kirsten rat sarcoma viral oncogene homolog) and/or SHH (Sonic Hedgehog), (ii) an mRNA molecule which encodes an anti-apoptotic protein (e.g., Bcl-xL, Bcl-2, survivin, Hax-1, AKT2, Mcl-1), or (iii) any other RNA molecule that inhibits or enhances expression of a protein that is associated with cancer.

In another embodiment, the nucleic acid molecule is an mRNA molecule that is expressed intracellularly as part of a therapeutic or diagnostic payload. Alternatively, the mRNA component may include a cDNA molecule. Further, the mRNA component may express a full wild type protein or peptide in a target cell, or may express at least the biologically active portion of the protein or peptide. When expressed within the target cell, the mRNA molecule acts as a therapeutic agent by expressing a protein or peptide that is missing or altered in the target cell, a cytotoxic protein or peptide to kill the target cell, an apoptotic triggering protein or peptide, or any other anti-cancer protein or peptide.

Chemotherapeutic agents that may be used in accordance with the embodiments described herein are often cytotoxic or cytostatic in nature and may include, but are not limited to, alkylating agents, antimetabolites, anti-tumor antibiotics, topoisomerase inhibitors, mitotic inhibitors hormone therapy, targeted therapeutics and immunotherapeutics. In some embodiments the chemotherapeutic agents that may be used as therapeutic agents in accordance with the embodiments of the disclosure include, but are not limited to, 13-cis-Retinoic Acid, 2-Chlorodeoxyadenosine, 5-Azacitidine, 5-Fluorouracil, 6-Mercaptopurine, 6-Thioguanine, actinomycin-D, adriamycin, aldesleukin, alemtuzumab, alitretinoin, all-transretinoic acid, alpha interferon, altretamine, amethopterin, amifostine, anagrelide, anastrozole, arabinosylcytosine, arsenic trioxide, amsacrine, aminocamptothecin, aminoglutethimide, asparaginase, azacytidine, *bacillus* calmette-guerin (BCG), bendamustine, bevacizumab, bexarotene, bicalutamide, bortezomib, bleomycin, busulfan, calcium leucovorin, citrovorum factor, capecitabine, canertinib, carboplatin, carmustine, cetuximab, chlorambucil, cisplatin, cladribine, cortisone, cyclophosphamide, cytarabine, darbepoetin alfa, dasatinib, daunomycin, decitabine, denileukin diftitox, dexamethasone, dexasone, dexrazoxane, dactinomycin, daunorubicin, decarbazine, docetaxel, doxorubicin, doxifluridine, eniluracil, epirubicin, epoetin alfa, erlotinib, everolimus, exemestane, estramustine, etoposide, filgrastim, fluoxymesterone, fulvestrant, flavopiridol, floxuridine, fludarabine, fluorouracil, flutamide, gefitinib, gemcitabine, gemtuzumab ozogamicin, goserelin, granulocyte-colony stimulating factor, granulocyte macrophage-colony stimulating factor, hexamethylmelamine, hydrocortisone hydroxyurea, ibritumomab, interferon alpha, interleukin-2, interleukin-11, isotretinoin, ixabepilone, idarubicin, imatinib mesylate, ifosfamide, irinotecan, lapatinib, lenalidomide, letrozole, leucovorin, leuprolide, liposomal Ara-C, lomustine, mechlorethamine, megestrol, melphalan, mercaptopurine, mesna, methotrexate, methylprednisolone, mitomycin C, mitotane, mitoxantrone, nelarabine, nilutamide, octreotide, oprelvekin, oxaliplatin, paclitaxel, pamidronate, pemetrexed, panitumumab, PEG Interferon, pegaspargase, pegfilgrastim, PEG-L-asparaginase, pentostatin, plicamycin, prednisolone, prednisone, procarbazine, raloxifene, rituximab, romiplostim, ralitrexed, sapacitabine, sargramostim, satraplatin, sorafenib, sunitinib, semustine, streptozocin, tamoxifen, tegafur, tegafur-uracil, temsirolimus, temozolamide, teniposide, thalidomide, thioguanine, thiotepa, topotecan, toremifene, tositumomab, trastuzumab, tretinoin, trimitrexate, alrubicin, vincristine, vinblastine, vindestine, vinorelbine, vorinostat, or zoledronic acid.

Therapeutic antibodies and functional fragments thereof, that may be used as therapeutic agents in accordance with the embodiments of the disclosure include, but are not limited to, alemtuzumab, bevacizumab, cetuximab, edrecolomab, gemtuzumab, ibritumomab tiuxetan, panitumumab, rituximab, tositumomab, and trastuzumab and other antibodies associated with specific diseases listed herein.

Toxins that may be used as therapeutic agents in accordance with the embodiments of the disclosure include, but are not limited to, ricin, abrin, ribonuclease (RNase), DNase I, Staphylococcal enterotoxin-A, pokeweed antiviral protein, gelonin, diphtheria toxin, *Pseudomonas* exotoxin, and *Pseudomonas* endotoxin.

Radioisotopes that may be used as therapeutic agents in accordance with the embodiments of the disclosure include, but are not limited to, $^{32}P$, $^{89}Sr$, $^{98}Y$, $^{99m}Tc$, $^{99}Mo$, $^{131}I$, $^{153}Sm$, $^{177}Lu$, $^{186}Re$, $^{213}Bi$, $^{223}Ra$ and $^{225}Ac$.

According to other embodiments, the pancreatic cell aptamers described herein may be conjugated to one or more diagnostic agents (or "imaging agents"), forming a diagnostic aptamer conjugate. The diagnostic aptamer conjugate may to target and visualize pancreatic cells in vivo via an imaging method (e.g., positron emission tomography (PET), computer assisted tomography (CAT), single photon emission computerized tomography, x-ray, fluoroscopy, and magnetic resonance imaging (MRI)). As such, the diagnostic aptamer conjugate may be used in methods for diagnosing, monitoring and/or visualizing a disease related to the pancreas.

In some embodiments, a diagnostic or imaging agent may include, but is not limited to a fluorescent, luminescent, or magnetic protein, peptide or derivatives thereof (e.g., genetically engineered variants). Fluorescent proteins that may be used include, but are not limited to, green fluorescent protein (GFP), enhanced GFP (EGFP), red, blue, yellow, cyan, and sapphire fluorescent proteins, and reef coral fluorescent protein. Luminescent proteins that may be used include, but are not limited to, luciferase, aequorin and derivatives thereof. Numerous fluorescent and luminescent dyes and proteins are known in the art (see, e.g., U.S. Patent Application Publication 2004/0067503; Valeur, B., "Molecular Fluorescence: Principles and Applications," John Wiley and Sons, 2002; Handbook of Fluorescent Probes and Research Products, Molecular Probes, 9.sup.th edition, 2002; and The Handbook—A Guide to Fluorescent Probes and Labeling Technologies, Invitrogen, 10th edition, available at the Invitrogen web site; both of which are hereby incorporated by reference as if fully set forth herein.)

In other aspects, a pancreatic cell aptamer may be further conjugated to or otherwise associated with a non-protein diagnostic agent or a delivery vehicle such as a nanoparticle, radioactive substances (e.g., radioisotopes, radionuclides, radiolabels or radiotracers), dyes, contrast agents, fluorescent compounds or molecules, bioluminescent compounds or molecules, enzymes and enhancing agents (e.g., paramagnetic ions). In addition, it should be noted that some nanoparticles, for example quantum dots and metal nanoparticles (described below) may also be suitable for use as a diagnostic agent or a therapeutic agent (e.g., using hyperthermal and photodynamic therapies as well as diagnostic agents through fluorescence and or MRI contrast).

Fluorescent and luminescent substances that may be used as an additional diagnostic agent in accordance with the embodiments of the disclosure include, but are not limited to, a variety of organic or inorganic small molecules commonly referred to as "dyes," "labels," or "indicators." Examples include fluorescein, rhodamine, acridine dyes, Alexa dyes, and cyanine dyes.

Enzymes that may be used as an additional diagnostic agent in accordance with the embodiments of the disclosure include, but are not limited to, horseradish peroxidase, alkaline phosphatase, acid phosphatase, glucose oxidase, β-galactosidase, β-glucoronidase or β-lactamase. Such enzymes may be used in combination with a chromogen, a fluorogenic compound or a luminogenic compound to generate a detectable signal.

Radioactive substances that may be used as an additional diagnostic agent in accordance with the embodiments of the disclosure include, but are not limited to, $^{18}F$, $^{32}P$, $^{33}P$, $^{45}Ti$, $^{47}Sc$, $^{52}Fe$, $^{59}Fe$, $^{62}Cu$, $^{64}Cu$, $^{67}Cu$, $^{67}Ga$, $^{68}Ga$, $^{77}As$, $^{86}Y$, $^{90}Y$, $^{89}Sr$, $^{89}Zr$, $^{94}Tc$, $^{94}Tc$, $^{99m}Tc$, $^{99}Mo$, $^{105}Pd$, $^{105}Rh$, $^{111}Ag$, $^{111}In$, $^{123}I$, $^{124}I$, $^{125}I$, $^{131}I$, $^{142}Pr$, $^{143}Pr$, $^{149}Pm$, $^{153}Sm$, $^{154-158}Gd$, $^{161}Tb$, $^{166}Dy$, $^{166}Ho$, $^{169}Er$, $^{175}Lu$, $^{177}Lu$, $^{186}Re$, $^{188}Re$, $^{189}Re$, $^{194}Ir$, $^{198}Au$, $^{199}Au$, $^{211}At$, $^{211}Pb$, $^{212}Bi$, $^{212}Pb$, $^{213}Bi$, $^{223}Ra$ and $^{225}Ac$. Paramagnetic ions that may be used as an additional diagnostic agent in accordance with the embodiments of the disclosure include, but are not limited to, ions of transition and lanthanide metals (e.g., metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

When the diagnostic agent is a radioactive metal or paramagnetic ion, the agent may be reacted with another long-tailed reagent having a long tail with one or more chelating groups attached to the long tail for binding these ions. The long tail may be a polymer such as a polylysine, polysaccharide, or other derivatized or derivatizable chain having pendant groups to which may be added for binding to the metals or ions. Examples of chelating groups that may be used according to the disclosure include, but are not limited to, ethylenediaminetetraacetic acid (EDTA), diethylenetriaminepentaacetic acid (DTPA), DOTA, NOTA, NETA, porphyrins, polyamines, crown ethers, bis-thiosemicarbazones, polyoximes, and like groups. The chelate is normally linked to the PSMA antibody or functional antibody fragment by a group which enables the formation of a bond to the molecule with minimal loss of immunoreactivity and minimal aggregation and/or internal cross-linking. The same chelates, when complexed with non-radioactive metals, such as manganese, iron and gadolinium are useful for MRI, when used along with the antibodies and carriers described herein. Macrocyclic chelates such as NOTA, DOTA, and TETA are of use with a variety of metals and radiometals including, but not limited to, radionuclides of gallium, yttrium and copper, respectively. Other ring-type chelates such as macrocyclic polyethers, which are of interest for stably binding nuclides, such as $^{223}Ra$ for RAIT may be used. In certain embodiments, chelating moieties may be used to attach a PET diagnostic agent, such as an Al—$^{18}F$ complex, to a targeting molecule for use in PET analysis.

In other embodiments, the aptamers may be conjugated to both a therapeutic and a diagnostic agent. Therefore, any of the above diagnostic and therapeutic agents may be used in combination to form an aptamer conjugate that targets pancreatic cells to deliver both a diagnostic and a therapeutic payload with a single dose.

Therapeutic Uses of Pancreatic Cancer Cell Aptamers

The aptamers and the aptamer-therapeutic agent conjugates described herein have at least a dual function that provides a basis for treating pancreatic cancer. First, according to some embodiments, the pancreatic cell aptamers may be used on their own to inhibit or suppress proliferation and survival of pancreatic cancer cells, and may also be used to eradicate existing primary or metastatic tumors.

Therefore, methods for suppressing pancreatic cancer cell proliferation, eradicating pancreatic cancer cell tumors and treating a pancreatic cancer or a pancreatic cancer cell malignancy, are provided according to the embodiments described herein. Pancreatic cancers and tumors that may be treated using the methods described herein include, but are not limited to acinar cell carcinoma, adenocarcinoma, adenosquamous carcinoma, giant cell tumor, intraductal papillary-mucinous neoplasm (IPMN), musinous cystadenocarcinoma, pancreatoblastoma, serous cystadenocarcinoma, solid and pseudopapillary tumors, gastrinoma (Zollinger-Ellison Syndrome), glucagonoma, insulinoma, nonfunctional islet cell tumors, somatostatinoma, secondary tumors derived from multiple endocrine neoplasia Type-1, or vasoactive intestinal peptide-releasing tumor (VIPoma or Verner-Morrison Syndrome).

"Treating" or "treatment" of a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof. For example, an aptamer or an aptamer conjugate such as those described herein may be used to treat pancreatic cancer, wherein the treatment refers to suppression of pancreatic cancer cell proliferation rate, an increase in pancreatic cancer cell death, or a decreased tumor size resulting in regression or eradication of a tumor. The treatments described herein may be used in any suitable subject, including a human subject or any mammalian or avian subject that needs treatment in accordance with the methods described herein (e.g., dogs, cats, horses, rabbits, mice, rats, pigs, cows).

The methods for treating the pancreatic cancer include administering a therapeutically effective amount of a therapeutic composition. An "effective amount," "therapeutically effective amount" or "effective dose" is an amount of a composition (e.g., a therapeutic composition or agent) that produces a desired therapeutic effect in a subject, such as preventing or treating a target condition or alleviating symptoms associated with the condition. The precise therapeutically effective amount is an amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. For additional guidance, see Remington: The Science and Practice of Pharmacy 21$^{st}$ Edition, Univ. of Sciences in Philadelphia (USIP), Lippincott Williams & Wilkins, Philadelphia, Pa., 2005.

The therapeutic composition may include, among other things, an aptamer, a therapeutic agent, an aptamer-therapeutic agent or a combination thereof. Aptamers, therapeutic agents, and aptamer-therapeutic agents suitable for use according to the embodiments described herein may include, but are not limited to, those described above and in the Examples below. For example, in some embodiments, an RNA aptamer that may be used as part of the therapeutic composition may include a sequence of SEQ ID NO:8. In other embodiments, the RNA aptamer may include a sequence of SEQ ID NO:1, SEQ ID NO:2, SEQ ID NO:3, SEQ ID NO:4, SEQ ID NO:5, or SEQ ID NO:6 (FIGS. 2A-2F).

The therapeutic composition may also include one or more pharmaceutically acceptable carriers. A "pharmaceutically acceptable carrier" refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or some combination thereof. Each component of the carrier must be "pharmaceutically acceptable" in that it must be compatible with the other ingredients of the formulation. It also must be suitable for contact with any tissue, organ, or portion of the body that it may encounter, meaning that it must not carry a risk of toxicity, irritation, allergic response, immunogenicity, or any other complication that excessively outweighs its therapeutic benefits.

The therapeutic compositions described herein may be administered by any suitable route of administration. A route of administration may refer to any administration pathway known in the art, including but not limited to aerosol, enteral, nasal, ophthalmic, oral, parenteral, rectal, transdermal (e.g., topical cream or ointment, patch), or vaginal. "Transdermal" administration may be accomplished using a topical cream or ointment or by means of a transdermal patch. "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal.

According to the embodiments described herein, the pharmaceutical composition may optionally include, in addition to the one or more aptamer or aptamer conjugates, one or more additional therapeutic agents, such as an anti-cancer agent, antibiotic, anti-viral agent, anti-HIV agent, anti-parasite agent, anti-protozoal agent, anesthetic, anticoagulant, inhibitor of an enzyme, steroidal agent, steroidal or non-steroidal anti-inflammatory agent, antihistamine, immunosuppressant agent, anti-neoplastic agent, antigen, vaccine, antibody, decongestant, sedative, opioid, analgesic, antipyretic, birth control agent, hormone, prostaglandin, progestational agent, anti-glaucoma agent, ophthalmic agent, anticholinergic, analgesic, anti-depressant, anti-psychotic, neurotoxin, hypnotic, tranquilizer, anti-convulsant, muscle relaxant, anti-Parkinson agent, anti-spasmodic, muscle contractant, channel blocker, miotic agent, anti-secretory agent, anti-thrombotic agent, anticoagulant, anti-cholinergic, .beta.-adrenergic blocking agent, diuretic, cardiovascular active agent, vasoactive agent, vasodilating agent, anti-hypertensive agent, angiogenic agent, modulators of cell-extracellular matrix interactions (e.g. cell growth inhibitors and anti-adhesion molecules), inhibitors of DNA, RNA, or protein synthesis.

In addition to their independent function for treating pancreatic cancer, the pancreatic cell aptamers may also serve as a pancreatic cell specific targeting delivery vehicle to deliver a therapeutic or diagnostic payload to a particular cell. Therefore, according to some embodiments, methods for delivering a therapeutic payload (or a therapeutic agent) to a pancreatic cancer cell are provided. Such methods may include a step of contacting the pancreatic cancer cell with a pancreatic cancer cell aptamer conjugate, wherein the pancreatic cell aptamer conjugate comprises a pancreatic cell aptamer component and a therapeutic agent component (i.e., the therapeutic payload). As described above, the pancreatic cell aptamer component may be any suitable aptamer, for example, a nucleic acid aptamer. In one embodiment, the nucleic acid aptamer is an RNA molecule that specifically binds a pancreatic cancer cell surface protein or other molecule, resulting in internalization of the pancreatic cell aptamer conjugate by the pancreatic cancer cell.

In one embodiment, the therapeutic agent component (or the therapeutic payload) may be an siRNA molecule, an miRNA molecule, an shRNA molecule, or an mRNA molecule as described with respect to aptamer-RNA chimeras described herein.

In another aspect, the pancreatic cell aptamer or aptamer conjugates may be used to deliver a diagnostic payload to pancreatic cancer cells or a pancreatic tumor cell. In such aspects, the pancreatic cell aptamer or aptamer conjugate may be used in methods of diagnosing pancreatic cancer. The methods for diagnosing a pancreatic cancer or pancreatic malignancy may include a step of administering to a subject suspected of having a pancreatic cancer or a pancreatic cancer malignancy, an effective amount of a pancreatic cancer cell aptamer that is conjugated to a diagnostic agent. The diagnostic agent may include one or more diagnostic agents, such as those described above. The method may further include a step of subjecting the subject to a diagnostic imaging technique (e.g., MRI, PET, CT, SPECT, PET/CT, PET/MRI, or other suitable imaging method) to visualize any diagnostic agent that is delivered to pancreatic cancer cells. Visualization of a diagnostic agent localized to an organ that is susceptible to pancreatic cancer (primary or metastatic cancer) such as the pancreas or liver, by the diagnostic imaging technique indicate that the subject has or likely has a form of pancreatic cancer such as those described above.

The following examples are intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

EXAMPLES

Aptamers that are identified using systematic evolution of ligands by exponential enrichment (SELEX) as an in vitro selection strategy can adopt complex structures to bind target proteins with high affinities and specificities (Ellington & Szostak 1990; Tuerk 1997). As described above, aptamers may be selected to recognize a wide variety of targets from small molecules to proteins and nucleic acids in cultured cells and whole organisms (Ulrich et al. 2002; Wang et al. 2000; Blank et al. 2001; Daniels et al. 2003; Hicke et al. 2001; Wilson & Szostak 1999). The Example below describes a cell-based SELEX assay for the identification of pancreatic cancer cell surface biomarkers and the therapeutic delivery of siRNAs into pancreatic cancer cells.

In the Examples described below, a 2'-fluropyrimidine-RNA (2'F-RNA) combinatorial library was used to isolate 2'F RNA aptamers against a Panc-1 cell line, which is an aggressive pancreatic cancer cell type. We observed that the aptamers selectively internalized into pancreatic cancer cells and the selected aptamers are candidates for targeted delivery of therapeutic siRNAs and other agents into these cells.

Example 1

Generation of Pancreatic Cell Aptamers for Use in Therapeutic Methods

Materials and Methods
Cell Lines.

To use intact cells as target, Panc-1 (CRL-1469), Capan-1 (HTB-79), CFPAC-1 (CRL-1918), MIA PaCa-2 (CRL-1420), BxPC-3 (CRL-1687) and AsPC-1 (CRL-1682) were purchased from ATCC for use as target intact cells and Huh7 cells were purchased from JCRB. Primary human pancreatic epithelial cells were purchased in cell systems. The cells were cultured in a humidified 5% $CO_2$ incubator at 37° C. according to cell bank's instructions.

Whole-Cell SELEX (Systemic Evolution of Ligands by Exponential Enrichment).

The SELEX cycle was performed as described by Tuerk and Gold (11). In vitro selection was carried out as described (Hwang et al. 2009), with a few modifications in this study. The 2'F-RNA aptamers were selected from randomized sequences. A random library of RNA oligonucleotides which have a sequence of 5'-GGGAGAGCG-GAAGCGUGCUGGGCC-$N_{40}$-CAUAA CCCAGAG-GUGAUGGAUCCCCC-3' (SEQ ID NO:7) was constructed by in vitro transcription of synthetic DNA templates with NTPs (2'F UTP, 2'F CTP, GTP, ATP, Epicentre Biotechnologies, Madison, Wis.) and T7 RNA polymerase. $N_{40}$ represents 40 nucleotide (nt) sequences formed by equimolar incorporation of A, G, C, and U at each position. To increase the nuclease resistance, 2'F-Py RNAs were used. For the first round, 5.87 nmol of the RNA library was incubated with target cells (Panc-1) in 1 ml binding buffer (PBS W/O $Ca^{2+}$ and $Mg^{2+}$, 5 mM $MgCl_2$, 0.01% BSA) for 1 hour at room temperature with shaking. RNA molecules that bound to target cells were recovered, amplified by RT-PCR and in vitro transcription, and used in the following selection rounds. In subsequent rounds, the RNA concentration was reduced by 10-fold and incubation time was reduced to create a more stringent condition. To remove RNAs that non-specifically bind the target cells, the counter-selection was carried out at every 3rd round using Huh7 cells. After 14 rounds of SELEX, the resulting cDNAs were amplified. The amplified DNA was cloned and individual clones were identified by DNA sequencing. Structures of aptamers were predicted using MFOLD (Zuker 2003), available online using a salt correction algorithm and temperature correction for 25° C.

Results and Discussion

In Vitro Selection of RNA Aptamers to the Intact Target Cells.

The human pancreatic carcinoma cells (Panc-1) were used as target cells for the aptamer selection and the human hepatoma cell line (Huh7) was used for the counter-selection steps to remove non-pancreatic cancer cell specific aptamers. A library of 2' Fluroro pyrimidines RNAs (2'F RNA) were used to increase nuclease-resistance and enhance aptamer folding. To isolate 2'F RNA aptamers binding to intact cells, a library of approximately $4^{40}$ different 2'F RNA molecules, containing a 40-nt-long random sequence flanked by defined sequences, was screened by SELEX. After 14 cycles of selection, the highly enriched aptamer pools were cloned. The nucleotide sequences of 47 clones were determined.

Comparison of Individual Sequences and Structures.

Six different groups of aptamers (or "clones") (Groups I-VI) were selected. Each group represents a set of repeated sequences. After 14 rounds of selection, the sequences of 47 clones were identified and the frequencies of each of the six aptamer clones were shown as number, as shown in Table 1 below.

TABLE 1

Alignment and identification of RNA aptamers

| Group | Name | Sequences (Random sequence) | Frequency (%) |
|---|---|---|---|
| I | P15 | GGGAGACAAGAAUAAACGCUCAAAGUUGC GGCCCAACCGUUUAAUUCAGAAUAGUGUG AUGCCUUCGACAGGAGGCUCACAACAGGC (SEQ ID NO: 1) | 19 (9/47) |
| II | P19 | GGGAGACAAGAAUAAACGCUCAAUGGCGA AUGCCCGCCUAAUAGGGCGUUAUGACUUG UUGAGUUCGACAGGAGGCUCACAACAGGC (SEQ ID NO: 2) | 13 (6/47) |
| III | P1 | GGGAGACAAGAAUAAACGCUCAAUGCGCU GAAUGCCCAGCCGUGAAAGCGUCGAUUUC CAUCCUUCGACAGGAGGCUCACAACAGGC (SEQ ID NO: 3) | 13 (6/47) |
| IV | P11 | GGGAGACAAGAAUAAACGCUCAAAUGAUU GCCCAUUCGGUUAUGCUUGCGCUUCCUAA AGAGCUUCGACAGGAGGCUCACAACAGGC (SEQ ID NO: 4 | 9 (4/47) |
| V | P7 | GGGAGACAAGAAUAAACGCUCAAGGCCAU GUUGAAUGCCCAACUAAGCUUUGAGCUUU GGAGCUUCGACAGGAGGCUCACAACAGGC (SEQ ID NO: 5) | 6 (3/47) |
| VI | P6 | GGGAGACAAGAAUAAACGCUCAACAAUGG AGCGUUAAACGUGAGCCAUUCGACAGGAG GCUCACAACAGGC (SEQ ID NO: 6) | 4 (2/47) |

The six groups of aptamers had very different sequences, however, sequences P19, P1 and P7 contained a common motif, GAAUGCCC (SEQ ID NO: 8). Sequence P15 was found nine times and the length of the random region was 40 nucleotides (nt). Sequences P19 and P1 were found six times and the length of the random regions was 40 nt. Sequence P11 was found four times and P7 was found three times. Both also have 40 nt in the randomized region. Sequence P6 was found two times and the length of the randomized region length is 24 nt. Minimum energy structural analyses of the selected aptamers were carried out using Mfold (Zuker, 2003) (FIGS. 2A, 2B, 2C, 2D, 2E and 2F). As shown in FIGS. 2A-2F, the calculated secondary structures of the RNA aptamers contained several stem-loop regions.

Example 2

Cell-Specific Aptamer Delivery to Pancreatic Cancer for Use in Therapeutic Methods Materials and Methods In addition to those described in Example 1 above, the following materials and methods were also used to determine the ability of the aptamers to target cells Live Cell Confocal Imaging for Cell Internalization.

In order to test the internalization of the selected RNA aptamers in the target cells and other types of pancreatic cancer cells, the cells were grown in 35 mm glass bottom dishes (MatTek, Ashland, Mass., USA) with seeding at $1 \times 10^6$ cells in medium for 24 hrs. The RNAs were labeled with Cy3 using the Cy3 Silencer siRNA labeling kit (Ambion, TX, USA) following the manufacturer's instructions. Cy3-labeled RNAs at 100 nM were added to the cells and incubated for 1 hour. Following the incubation, the cells were stained with 5 ug/ml Hoechst 33342 (Molecular Probes, CA, USA) for live cell nuclear staining. The images were taken using a Zeiss LSM 510 Meta Inverted 2 photon confocal microscope system under water immersion at 40× magnification.

Binding Assay by Flow Cytometric Analysis.

Aptamer binding and uptake was also assessed by flow cytometry. For the assay, cells were detached using a non-enzymatic cell dissociation solution, washed with PBS and suspended in binding buffer. Next, Cy3-labeled aptamers were added and incubated for 1 hours at 37° C. The binding of individual aptamers or the starting pool as a control to pancreatic cancer cells was performed in triplicate. Flow cytometry was performed on a Guava (Millipore, Billerica, Mass., USA) flow cytometer and the data were analyzed with FlowJo software.

Binding Affinity and $K_D$ Determination.

To determine the binding affinity of aptamers to Panc-1, Kd function of physiology macro provided by a Zeiss LSM 510 Meta Inverted 2 photon confocal microscope system was used. The cells were grown in 35 mm glass bottom dishes (MatTek, Ashland, Mass., USA) with seeding at $1 \times 10^6$ cells in medium for 24 hrs. The RNAs were labeled with Cy3 using the Cy3 Silencer siRNA labeling kit (Ambion, TX, USA) following the manufacturer's instructions. Various concentrations of Cy3-labeled RNAs were added to the cells and incubated for 1 hour. After extensive washing, 20 images of each condition of a titration curve were taken. The dissociation constants were calculated using one site binding non-linear curve regression with a Graph Pad Prism.

Cell Internalization Competition Assays.

Panc-1 cells were prepared as detailed above for the confocal microscopy. 200 nM of Cy3 labeled P19 aptamer was used to compete with either unlabeled clones (1 μM) in 1× Binding buffer prewarmed at 37° C. Cells were washed three times and took images by confocal microscopy.

WST-1 Assay.

Cell proliferation was quantified following four treatments of P1 and P19 at 9 ug per treatment in Panc-1($2.5 \times 10^5$ cells), using WST-1 reagent following the manufacturer's guidelines (Roche, UK). Briefly, the WST-1 reagent was used at a 1:100 dilution to plates and incubated for one hour. The enzymatic reaction was measured at 450 ηm using Bio-Tek ELISA reader.

Animal Experiments.

Five NOD/SCID mice were injected subcutaneously (s.c.) on the flank with Panc-1 pancreatic cancer cells in 0.05 ml PBS with 0.15 ml Matrigel. After 2 weeks, mice were divided into two groups. One group served as untreated controls and the others injected 10 ug with P1 combined with P19. Aptamers were injected via tail vein (i.v.), for a total of 4 times per animal. Animals were sacrificed before tumour disappeared.

For the gemcitabine resistant tumour test, twelve 5-week-old female NOD/SCID mice were injected subcutaneously (S.C.) on the flank with $2.8 \times 10^6$ ASPC-1 pancreatic cancer cells in 0.05 ml PBS with 0.15 ml Matrigel. After 3 weeks, mice were divided into four groups. One group served as untreated controls and the others injected with P1 (10 ug per injection), P19 (10 ug per injection) and P1 combined with P19 (5 ug of P1 with 5 ug of P19 per injection). Aptamers were injected through tail vein (i.v.) for a total of 4 times per animal (at day 1, 3, 5, and 7). Animals were sacrificed at day 9.

Results

RNA Aptamers Specifically Bind to and are Internalized in Pancreatic Cancer Cells.

Figure 3:
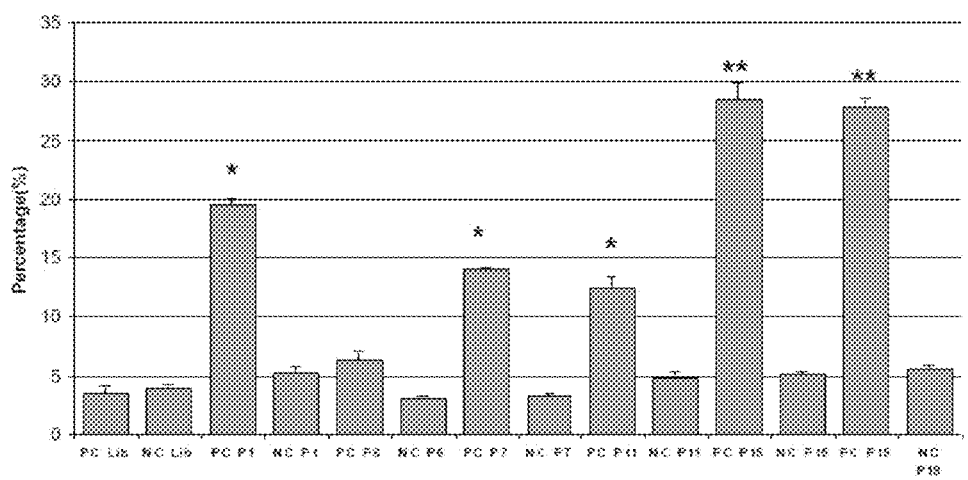
FIG. 3 illustrates cell-type specific binding and uptake by flow cytometry. Cy3-labeled RNAs were tested for binding to Panc-1 and Huh7 as control cells. The selected aptamers showed cell-type specific binding affinity. The results are reported as mean±S.D. Asterisks indicate that the value is significantly different from the value for the initial RNA library control in the corresponding assay, with P values of P=0.001(**) to 0.01(*). P values were calculated using a two-tailed, paired t-test with 95% confidence intervals. Data shown are the means of three replicates, and error bars represent the standard errors of the means. Data represent the average of three replicated. Initial RNA library pool is shown as Lib. PC; Panc-1, NC; Huh7.
Figure 4:
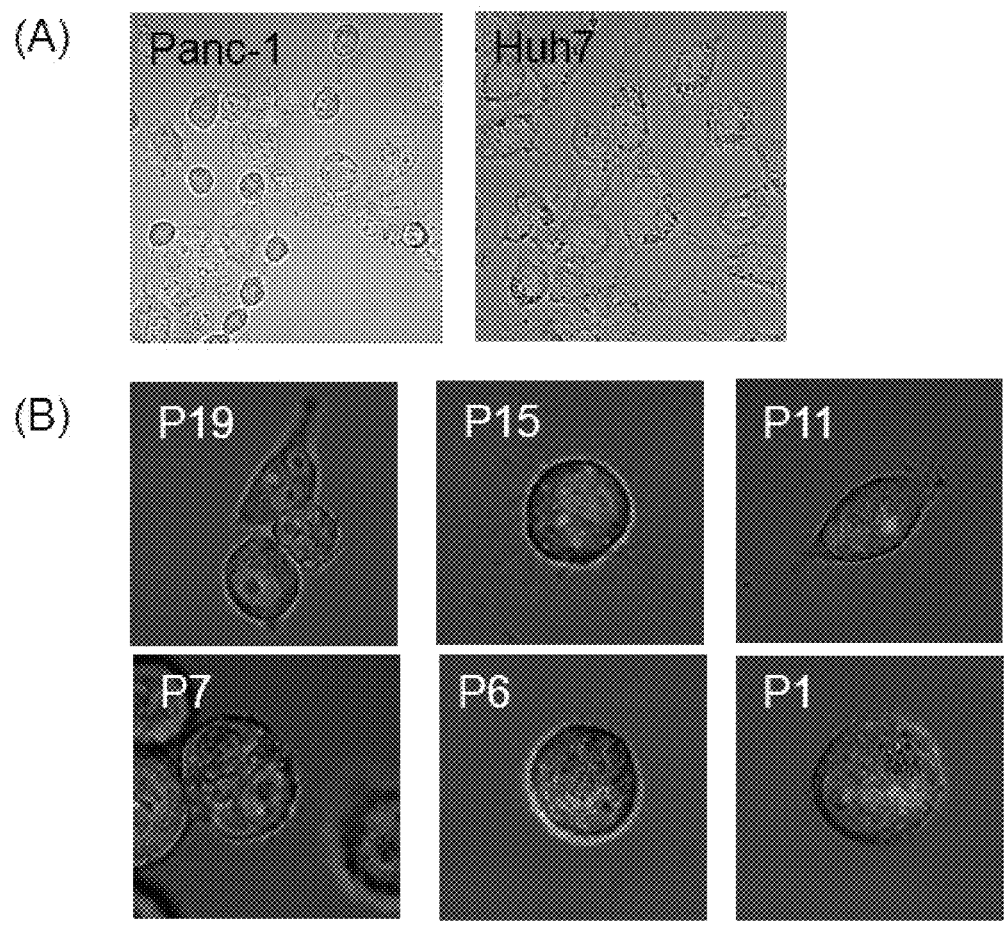
FIG. 4 illustrates cell-internalization of target cells by confocal microscopy. Cells were grown in 35 mm dishes and incubated with 100 nM of Cy3-labeled RNA. After one hour incubation, cells were washed and took images using 40× magnification. (A) Initial RNA library pool was incubated in Panc-1 and Huh7. (B) Each aptamer clones were incubated in Panc-1. Red; Cy3-labeled RNA, Blue: Hoechest 33342 (Nuclear dye for living cells).
Figure 5E:
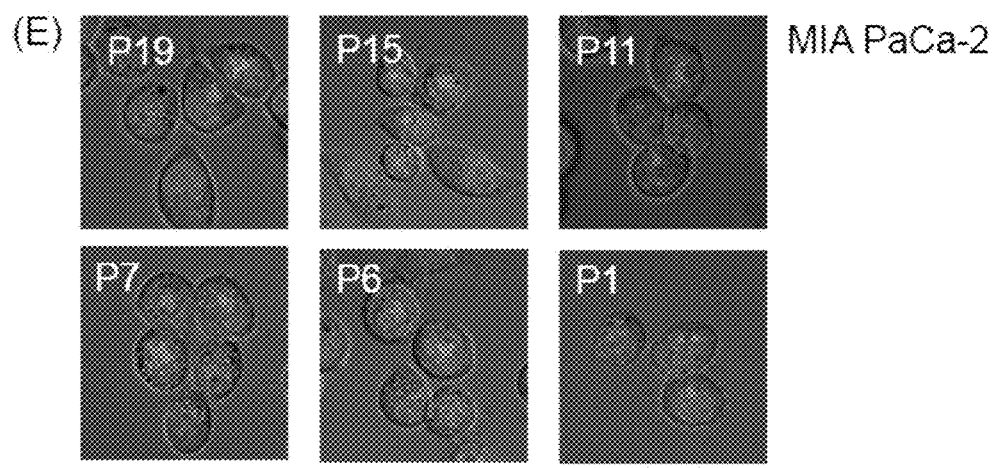
FIG. 5 illustrates cell-internalization in other types of pancreatic cancer cells by confocal microscopy. Each RNA aptamer clones labeled with Cy3 were applied to different type of pancreatic cancer cells. Cells were grown in 35 mm dishes and incubated with 100 nM of RNA. After one hour incubation, cells were washed and took images using 40× magnification. (A) AsPC-1. (B) CFPAC-1. (C) BxPC-1. (D) Capan-1. (E) MIA PaCa-2. Red; Cy3-labeled RNA, Blue: Hoechest 33342 (Nuclear dye for living cells). Aptamers were internalized by every type of pancreatic cancer cells.

Flow cytometric analyses of the individual clones revealed the aptamers bound to the target cells (FIG. 3). In order to determine that the selected six different aptamers were internalized in the pancreatic cancer cells, the live-cell confocal microscopy with the Cy3-labeled RNA transcripts was carried out. The RNA aptamers were internalized specifically in target cells Panc-1 (FIG. 4B), but not the Huh7 control cells (FIG. 4A). Non-specific weak binding was observed when initial the RNA library pool was incubated with Panc-1. FIG. 4B shows that the aptamers aggregate within the cytoplasm, suggesting that the RNA aptamers enter into cells via receptor-mediated endocytosis. To test that the aptamers recognize different type of pancreatic cancer cells, five different pancreatic cancer cell lines were tested for aptamer uptake. All six of the tested aptamers internalized in all the pancreatic cancer cells (FIGS. 5A, 5B, 5C, 5D, 5E).

As described above, a strategy for identifying RNA aptamers that target pancreatic cancer cells was developed and the selected RNA aptamers were demonstrated to internalize within the cells, indicating that the RNA aptamers described herein may be used as targeting agents to deliver therapeutic agents to pancreatic cancer cells, such as siRNAs or chemotherapy agents.

Figure 6A:
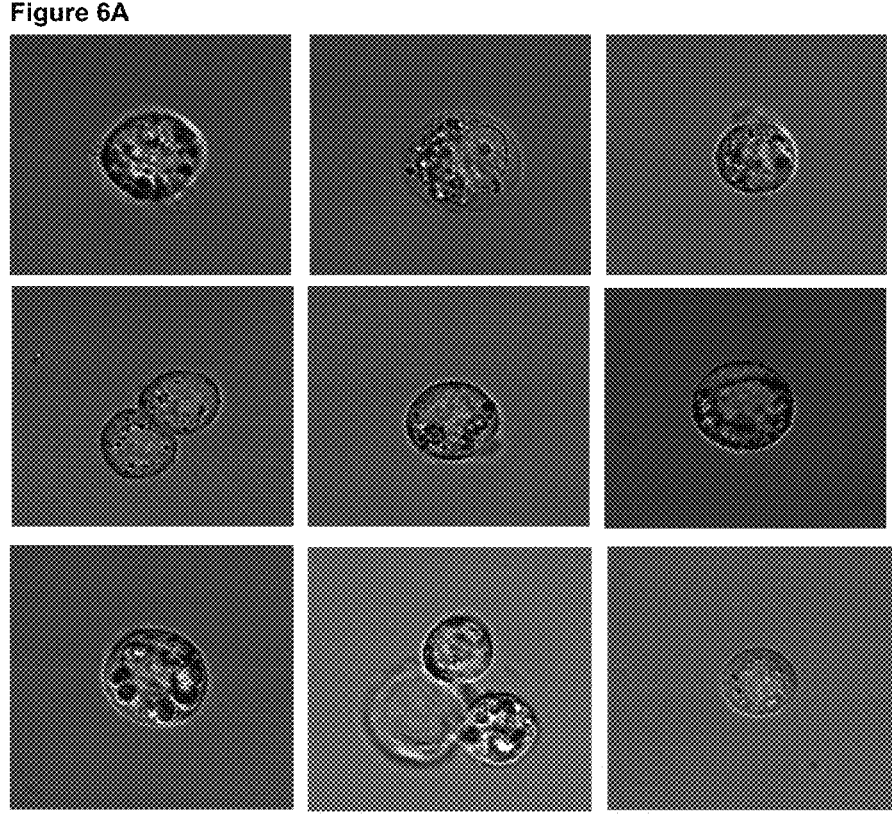
FIG. 6 illustrates cell-internalization in normal primary pancreatic cells by confocal microscopy. Each of the RNA aptamer clones labeled with Cy3 was applied to different type of normal pancreatic cells. Cells were grown in 35 mm dishes and incubated with 100 nM of RNA. After one hour incubation, cells were washed and took images using 40× magnification. Red: Cy3-labeled RNA (none shown), Blue: Hoechest 33342 (Nuclear dye for living cells). None of the normal pancreatic cancer cells internalized the RNA aptamers.
Figure 6B:
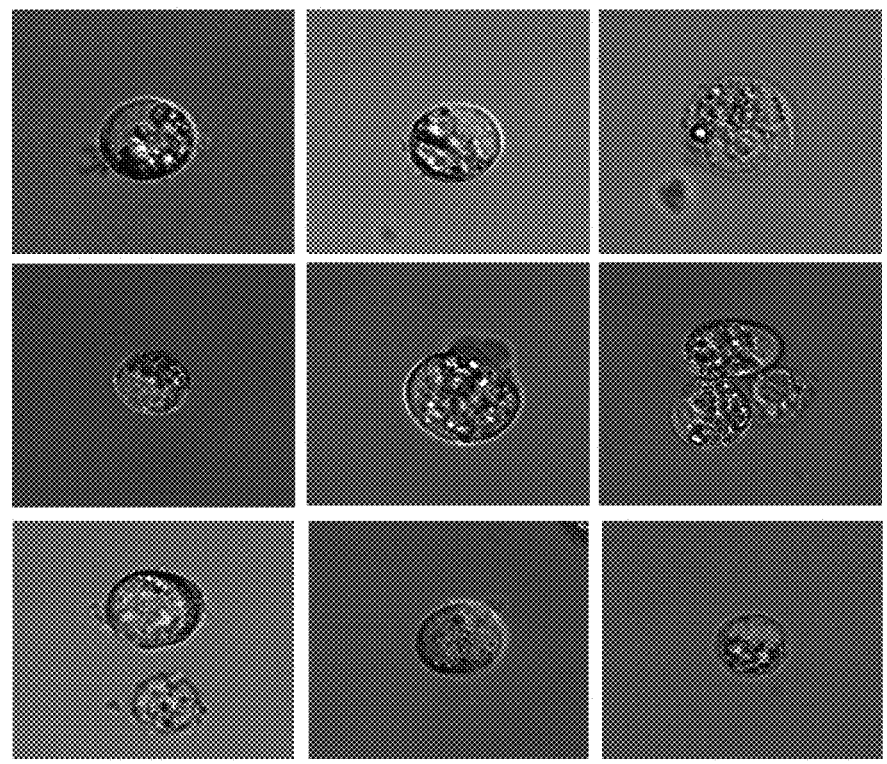

In contrast to pancreatic cancer cells, the aptamers are not internalized by normal pancreatic cells. To determine whether the selected aptamers bind to normal pancreatic cells, primary epithelial pancreatic cells were incubated with Cy3 labeled aptamers as described above. As shown in FIGS. 6A and 6B, none of the Cy3 labeled aptamers were internalized by the normal pancreatic cells, indicating that the aptamers bind specifically to a cell surface molecule (e.g., a cell surface protein) that is expressed on pancreatic cancer cells, but is not expressed on normal pancreatic cells.

RNA Aptamer Binding Affinity of Target Cells.

Figure 7:
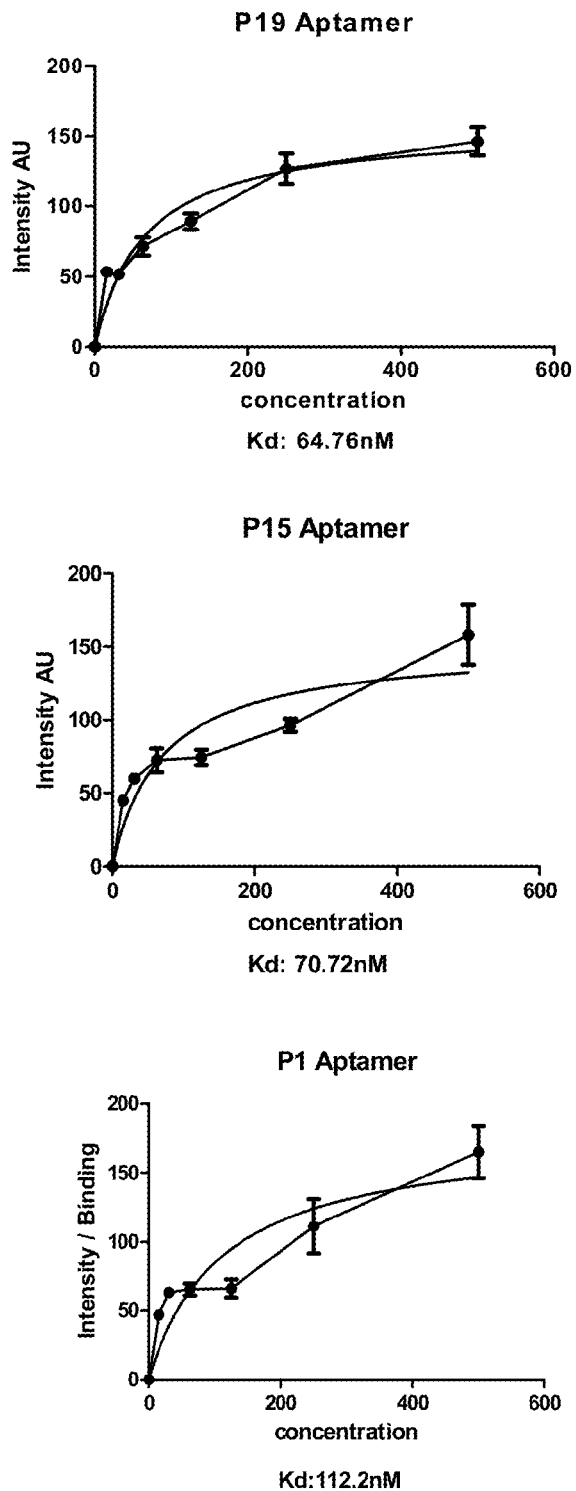
FIG. 7 shows the binding affinity of P19, P15 and P1 aptamers. The measurement of dissociation constant ($K_D$) was done by physiology function of Zeiss LSM using various concentrations (15.6-500 nM) of Cy3 labeled aptamers. The affinity of P19, P15, and P1 were 64.76 nM, 70.72 nM, and 112.2 nM, respectively.
Figure 8:
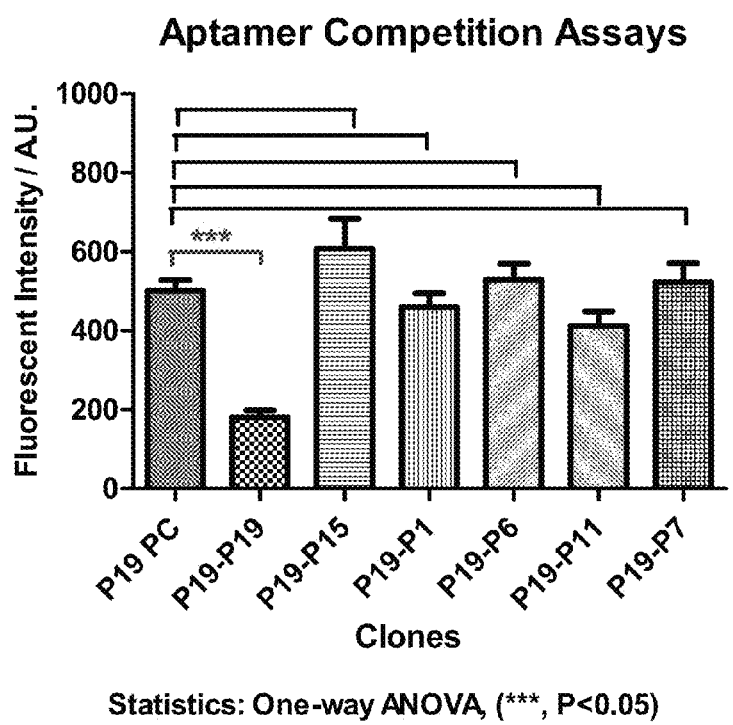
FIG. 8 illustrates cell internalization competition assays by confocal microscopy. Panc-1 cells were incubated with fluorescently labeled P19 RNA (200 nM) and increasing amounts (1 μM) of unlabeled each clone aptamers as competitors against the labeled RNA. The fluorescence intensity was quantified in the presence of increasing amounts of competitors using confocal microscopy and analyzed statistically.

To estimate the affinity of the RNA aptamers, Physiology function of confocal microscopy was utilized. The measured dissociation constants ($K_D$) of P19, P15, and P1 were 64.76 nM, 70.72 nM, and 112.2 nM, respectively (FIG. 7). To determine whether each aptamer binds to the pancreatic cancer cells via the same or different cell surface proteins, Panc-1 cells were incubated with fluorescently labeled P19 RNA (100 nM) and increasing amounts (1 μM) of each unlabeled aptamer as a competitor against the labeled chimeras (FIG. 8). The fluorescence intensity of labeled RNAs was measured in the presence of increasing amounts of competitors using confocal microscopy. The intensity of P19 competed with unlabeled P19 was significantly decreased (indicating competition for the same target); while others showed insignificant changes, indicating that each RNA aptamer has a different binding site on the same target or binds different targets.

The Anti-Tumor Effect of Selected RNA Aptamers.

Figure 9:
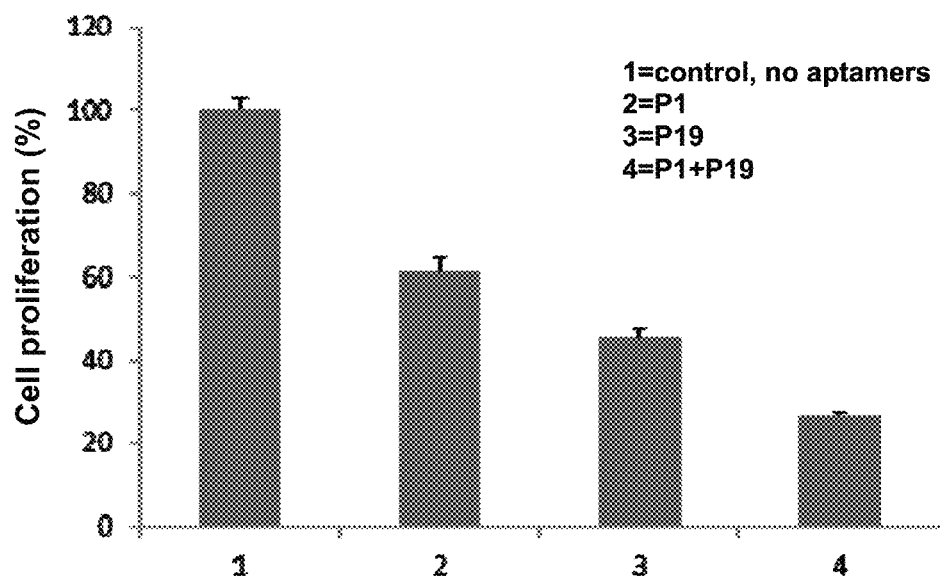
FIG. 9 shows cell proliferation assays for cells treated with P1 and P19 aptamers. Cell proliferation was quantified by WST-1 reagent following the manufacturer's guidelines. Panc-1 ($2.5 \times 10^5$ cells) was treated with four times of P1 and P19 at 9 ug per treatment in Panc-1. WST-1 reagent was used at a 1:100 dilution to plates and incubated for one hour. The enzymatic reaction was measured at 450 ηm using Bio-Tek ELISA reader
Figure 10:
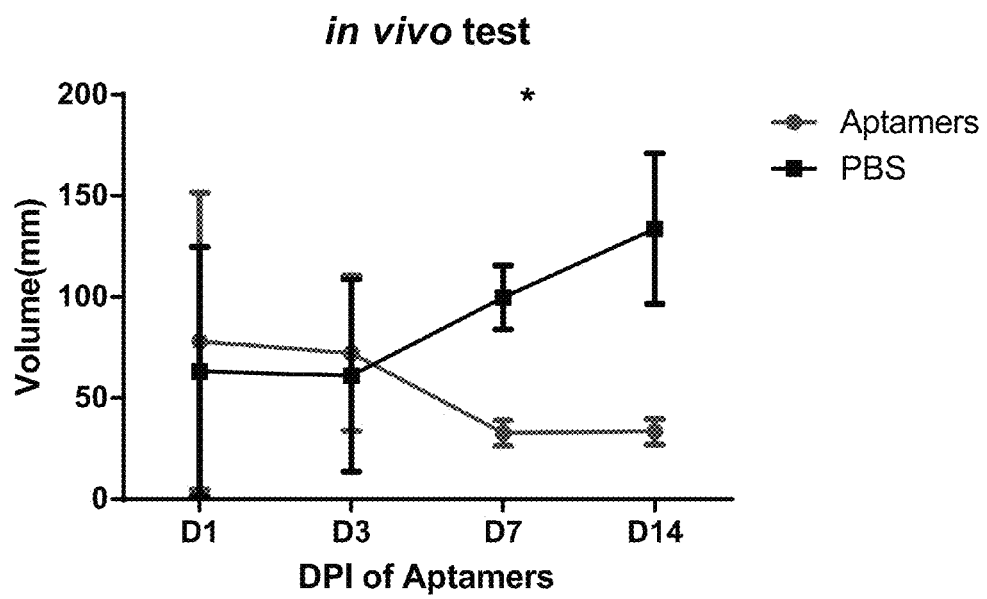
FIG. 10 illustrates results of in vivo experiments. Panc-1 pancreatic cancer cells were injected subcutaneously (s.c.) on the flank in five NOD/SCID mice. After 2 weeks, mice were divided into two groups. One group served as untreated controls and the others injected 10 ug with P1 combined with P19. Aptamers were injected via tail vein. A total of 4 times was injected per animal. Student t-test was used for statistical analysis. * TTEST: P value <0.05.
Figure 11:
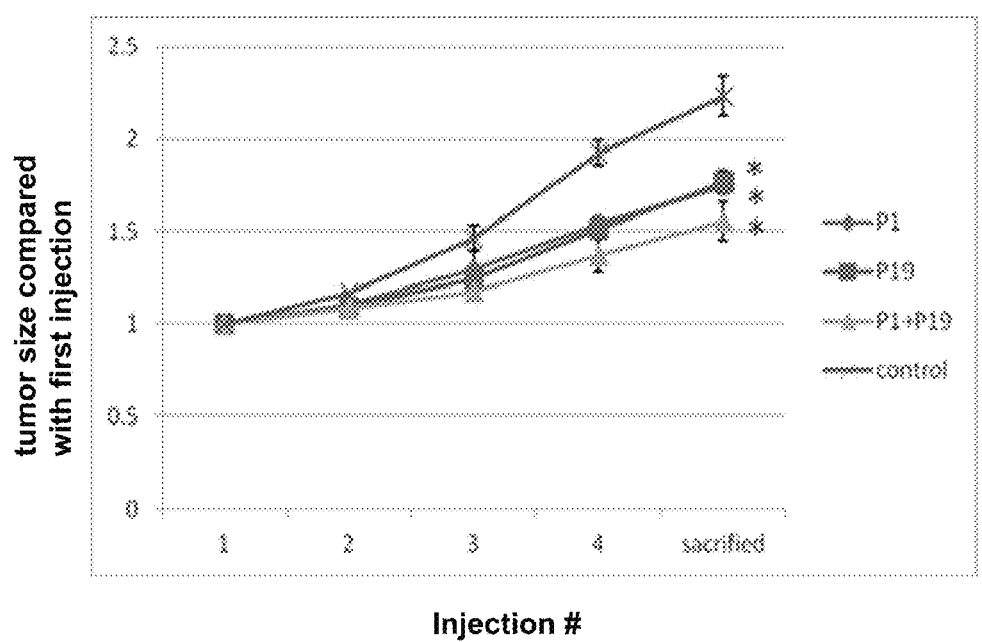
FIG. 11 illustrates results of gemcitabine-resistant tumor animal experiments. Gemcitabine-resistant ASPC-1 ($2.8 \times 10^6$) cells were injected subcutaneously (s.c.) on the flank in twelve 5-weeks-old female NOD/SCID mice. After 3 weeks, mice were divided into four groups. One group served as untreated controls and the others injected with P1, P19, and P1 combined with P19 (P1+P19). Aptamers were injected via tail vein. A total of 4 times was injected per animal every two days and sacrificed at day 9. When compared to the control, all three treatment groups showed a significant anti-tumor effect (*P<0.05)

To evaluate anti-tumor effect, three aptamer clones (P19, P15 and P1) were injected into SCID mice intravenously (i.v.). P19 and P1 inhibited cell proliferation in vitro (FIG. 9). P19 and P1 also significantly reduced the tumor size in Panc-1 engrafted mice when administered via i.v. injection (FIG. 10), even in gemcitabine resistant pancreatic cancer (FIG. 11). Based on these results, the selected P19 and P1 aptamers may be used as an effective for pancreatic cancer on their own due to their anti-cancer, tumor regressing effects. Further, because it was shown that the P19 and P1 aptamers effectively target and are internalized by pancreatic cancer cells, they also have a dual function in that they can deliver a payload (e.g., a therapeutic agent) to the pancreatic cancer cells, resulting in an additional anti-cancer effect.

As such, the P19 and P1 aptamers may be used as delivery agents for delivery of one or more therapeutic agents that target K-ras (V-Ki-ras2 Kirsten rat sarcoma viral oncogene homolog) and SHH (Sonic Hedgehog) according to some embodiments. By utilizing both their independent anti-tumor effect as well as their ability to deliver a therapeutic payload, the anti-tumour effects of P19 and P1 aptamers will likely be increased as compared to their ability to deliver a therapeutic payload alone.

Additionally, it has been shown that pancreatic cancer cells may spread to the liver even at the pre-neoplastic stage (Rhim et al. 2012). As such, intravenous administration of the aptamers for use as a systemic therapy is particularly important in that the vast majority of patients with pancreatic cancer, since most likely, the patients have distant tumour spread at the time of diagnosis. In that vein, the specific RNA aptamers against pancreatic cancer may be used as part of a drug or a pharmaceutical composition for systemic therapy, and may also be used for diagnosis and staging of pancreatic cancer.

In conclusion, as illustrated in the Examples above, a strategy for identifying RNA aptamers that target pancreatic cancer cells has been developed, and the selected RNA aptamers were shown to internalize within the cells. Further, RNA aptamers themselves were shown to have anti-tumor effect on their own, and also specifically target pancreatic cancer cells—not normal pancreatic cells. This provides an advantage for a clinical application for early detection of pancreatic cancer and treatment by targeting pancreatic cancer cells. Thus, the RNA aptamers described herein may be used as targeting agents to deliver therapeutic agents (e.g., siRNA or chemotherapeutics) or diagnostic agents to pancreatic cancer cells.

REFERENCES

The references, patents and published patent applications listed below, and all references cited in the specification above are hereby incorporated by reference in their entirety, as if fully set forth herein.

Alexakis, N., et al. Current standards of surgery for pancreatic cancer. *The British journal of surgery* 91, 1410-1427 (2004).
Blank, M., Weinschenk, T., Priemer, M. and Schluesener, H. (2001) Systematic evolution of a DNA aptamer binding to rat brain tumor microvessels. selective targeting of endothelial regulatory protein pigpen. *J Biol Chem*, 276, 16464-16468.
Cunningham, D., et al. Phase III randomized comparison of gemcitabine versus gemcitabine plus capecitabine in patients with advanced pancreatic cancer. *Journal of clinical oncology: official journal of the American Society of Clinical Oncology* 27, 5513-5518 (2009).
Daniels, D. A., Chen, H., Hicke, B. J., Swiderek, K. M. and Gold, L. (2003) A tenascin-C aptamer identified by tumor cell SELEX: systematic evolution of ligands by exponential enrichment. *Proc Natl Acad Sci USA*, 100, 15416-15421.
Ellington, A. D. and Szostak, J. W. (1990) In vitro selection of RNA molecules that bind specific ligands. *Nature*, 346, 818-822.
Esposito et al. A Neutralizing RNA Aptamer against EGFR Causes Selective Apoptotic Cell Death. PLoS One. 2011; 6(9): e24071.
Fulda, S. (2009) Apoptosis pathways and their therapeutic exploitation in pancreatic cancer. *J Cell Mol Med*, 13, 1221-1227.
Ghaneh, P., Costello, E. & Neoptolemos, J. P. Biology and management of pancreatic cancer. *Gut* 56, 1134-1152 (2007).
Guidelines for the management of patients with pancreatic cancer periampullary and ampullary carcinomas. *Gut* 54 Suppl 5, v1-16 (2005)
Heinemann, V., Haas, M. & Boeck, S. Systemic treatment of advanced pancreatic cancer. *Cancer treatment reviews* 38, 843-853 (2012).
Hicke, B. J., Marion, C., Chang, Y. F., Gould, T., Lynott, C. K., Parma, D., Schmidt, P. G. and Warren, S. (2001) Tenascin-C aptamers are generated using tumor cells and purified protein. *J Biol Chem*, 276, 48644-48654.
Hwang, B., Lim, J. H., Hahm, B., Jang, S. K. and Lee, S. W. (2009) hnRNP L is required for the translation mediated by HCV IRES. *Biochem Biophys Res Commun*, 378, 584-588.
Jemal, A., Siegel, R., Ward, E., Hao, Y., Xu, J. and Thun, M. J. (2009) Cancer statistics, 2009. *CA Cancer J Clin*, 59, 225-249.
Klinkenbijl, J. H., et al. Adjuvant radiotherapy and 5-fluorouracil after curative resection of cancer of the pancreas and periampullary region: phase III trial of the EORTC gastrointestinal tract cancer cooperative group. *Annals of surgery* 230, 776-782; discussion 782-774 (1999).
Li, D., Xie, K., Wolff, R. and Abbruzzese, J. L. (2004) Pancreatic cancer. *Lancet*, 363, 1049-1057.
Neoptolemos, J. P., et al. A randomized trial of chemoradiotherapy and chemotherapy after resection of pancreatic cancer. *The New England journal of medicine* 350, 1200-1210 (2004).
Oettle, H., et al. Adjuvant chemotherapy with gemcitabine vs observation in patients undergoing curative-intent resection of pancreatic cancer: a randomized controlled trial. *JAMA: the journal of the American Medical Association* 297, 267-277 (2007).
Pancreatic cancer in the UK. *Lancet* 378, 1050 (2011).
Rhim, A. D., Mirek, E. T., Aiello, N. M., Maitra, A., Bailey, J. M., McAllister, F., Reichert, M., Beatty, G. L., Rustgi, A. K., Vonderheide R. H., Leach S. D., Stanger B. Z. (2012) EMT and dissemination precede pancreatic tumor Formation. *Cell*, 148, 349-361.
Rivera, F., Lopez-Tarruella, S., Vega-Villegas, M. E. and Salcedo, M. (2009) Treatment of advanced pancreatic cancer: from gemcitabine single agent to combinations and targeted therapy. *Cancer Treat Rev*, 35, 335-339.
Saif, M. W. (2009) Adjuvant treatment of pancreatic cancer in 2009: where are we? Highlights from the 45th ASCO annual meeting. Orlando, Fla., USA. May 29-Jun. 2, 2009. *JOP*, 10, 373-377.
Schneider, G., Siveke, J. T., Eckel, F. and Schmid, R. M. (2005) Pancreatic cancer: basic and clinical aspects. *Gastroenterology*, 128, 1606-1625.
Sebolt-Leopold, J. S. and English, J. M. (2006) Mechanisms of drug inhibition of signalling molecules. *Nature*, 441, 457-462.
Stathis, A. and Moore, M. J. (2010) Advanced pancreatic carcinoma: current treatment and future challenges. *Nat Rev Clin Oncol*, 7, 163-172.
Tuerk, C. (1997) Using the SELEX combinatorial chemistry process to find high affinity nucleic acid ligands to target molecules. *Methods Mol Biol*, 67, 219-230.

Ulrich, H., Magdesian, M. N., Alves, M. J. and Colli, W. (2002) In vitro selection of RNA aptamers that bind to cell adhesion receptors of *Trypanosoma cruzi* and inhibit cell invasion. *J Biol Chem*, 277, 20756-20762.

Vincent, A., Herman, J., Schulick, R., Hruban, R. H. & Goggins, M. Pancreatic cancer. *Lancet* 378, 607-620 (2011).

Wang, J., Jiang, H. and Liu, F. (2000) In vitro selection of novel RNA ligands that bind human cytomegalovirus and block viral infection. *RNA*, 6, 571-583.

Wilson, D. S. & Szostak, J. W. (1999) In vitro selection of functional nucleic acids. *Annu Rev Biochem*, 68, 611-647.

Wong, H. H. and Lemoine, N. R. (2009) Pancreatic cancer: molecular pathogenesis and new therapeutic targets. *Nat Rev Gastroenterol Hepatol*, 6, 412-422.

Zuker, M. (2003) Mfold web server for nucleic acid folding and hybridizationprediction. *Nucleic Acids Res*, 31, 3406-3415.

Zhou J, Li H, Li S, Zaia J, Rossi J J. Novel dual inhibitory function aptamer-siRNA delivery system for HIV-1 therapy. *Mol Ther*. 2008; 16(8):1481-1489.

Zhou J, Rossi J J. The therapeutic potential of cell-internalizing aptamers. *Curr Top Med Chem*. 2009; 9(12):1144-1157.

---

What is claimed is:

1. A pancreatic cancer cell aptamer comprising an RNA molecule that specifically binds a pancreatic cancer cell surface protein, wherein the RNA molecule comprises the nucleotide sequence of SEQ ID NO:1, SEQ ID NO:2, SEQ ID NO:3, SEQ ID NO:4, SEQ ID NO:5, or SEQ ID NO:6.

2. The pancreatic cancer cell aptamer of claim 1, wherein the aptamer is conjugated to one or more therapeutic agents.

3. The pancreatic cancer cell aptamer of claim 2, wherein the one or more therapeutic agents are selected from an shRNA molecule, an siRNA molecule, an mRNA molecule, or an miRNA molecule.

4. The aptamer or claim 1, wherein the aptamer is conjugated to one or more diagnostic agents.

5. The pancreatic cancer cell aptamer of claim 4, wherein the one or more diagnostic agents are selected from a nanoparticle, a radioactive substance, a dye, a contrast agent, a fluorescent molecule, a bioluminescent molecule, an enzyme, or an enhancing agent.

6. The pancreatic cancer cell aptamer of claim 1, wherein the pancreatic cancer cell aptamer is part of a pharmaceutical composition which further comprises a pharmaceutical carrier.

7. The pancreatic cancer cell aptamer of claim 6, wherein the pharmaceutical composition further comprises one or more additional therapeutic agents.

8. A method of delivering a therapeutic agent to a pancreatic cancer cell comprising contacting the pancreatic cancer cell with a pancreatic cancer cell aptamer conjugate, wherein the pancreatic cancer cell aptamer conjugate comprises a pancreatic cancer cell aptamer component and a therapeutic agent component; and wherein the pancreatic cancer cell aptamer component is an RNA molecule which comprises the nucleotide sequence of SEQ ID NO:1, SEQ ID NO:2, SEQ ID NO:3, SEQ ID NO:4, SEQ ID NO:5, SEQ ID NO:6, or SEQ ID NO: 8, and which specifically binds a pancreatic cancer cell surface protein, resulting in internalization of the pancreatic cancer cell aptamer conjugate.

9. The method of claim 8, wherein the therapeutic agent component comprises an shRNA molecule, an siRNA molecule, an mRNA molecule, or an miRNA molecule.

10. The method of claim 8, wherein contacting the pancreatic cancer cell with a pancreatic cancer cell aptamer conjugate is accomplished by administering the pancreatic cancer cell aptamer conjugate to a subject intravenously.

11. A method for treating pancreatic cancer comprising administering a therapeutically effective amount of a pancreatic cancer cell aptamer, wherein the pancreatic cancer cell aptamer comprises an RNA molecule which comprises the nucleotide sequence of SEQ ID NO:1, SEQ ID NO:2, SEQ ID NO:3, SEQ ID NO:4, SEQ ID NO:5, SEQ ID NO:6, or SEQ ID NO: 8 and which specifically binds a pancreatic cancer cell surface protein, and wherein the pancreatic cancer cell aptamer prevents binding of a pancreatic cancer cell ligand.

12. The method of claim 11, wherein the pancreatic cancer cell aptamer is conjugated to one or more therapeutic agents.

13. The method of claim 12, wherein the one or more therapeutic agents are selected from an shRNA molecule, an siRNA molecule, an mRNA molecule, or an miRNA molecule.

14. The method of claim 11, wherein the pancreatic cancer is an acinar cell carcinoma, an adenocarcinoma, an adenosquamous carcinoma, a giant cell tumor, an intraductal papillary-mucinous neoplasm (IPMN), a musinous cystadenocarcinoma, pancreatoblastoma, a serous cystadenocarcinoma, a solid and pseudopapillary tumor, a gastrinoma (Zollinger-Ellison Syndrome), a glucagonoma, an insulinoma, a nonfunctional islet cell tumor, a somatostatinoma, a secondary tumor derived from multiple endocrine neoplasia Type-1, or a vasoactive intestinal peptide-releasing tumor.

15. A pharmaceutical composition comprising a pancreatic cancer cell aptamer, wherein the pancreatic cancer cell aptamer comprises: an RNA molecule that specifically binds a pancreatic cancer cell surface protein, and wherein the RNA molecule comprises the nucleotide sequence comprising SEQ ID NO:1, SEQ ID NO:2, SEQ ID NO:3, SEQ ID NO:4, SEQ ID NO:5, or SEQ ID NO:6; and a pharmaceutically acceptable carrier.

* * * * *

SEQUENCE LISTING

```
<160> NUMBER OF SEQ ID NOS: 8

<210> SEQ ID NO 1
<211> LENGTH: 87
<212> TYPE: RNA
<213> ORGANISM: Artificial Sequence
<220> FEATURE:
<223> OTHER INFORMATION: Synthetic oligonucleotide

<400> SEQUENCE: 1
gggagacaag aauaaacgcu caaaguugcg gcccaaccgu uuaauucaga auagugugau      60
gccuucgaca ggaggcucac aacaggc                                         87

<210> SEQ ID NO 2
<211> LENGTH: 87
<212> TYPE: RNA
<213> ORGANISM: Artificial Sequence
<220> FEATURE:
<223> OTHER INFORMATION: Synthetic oligonucleotide

<400> SEQUENCE: 2
gggagacaag aauaaacgcu caauggcgaa ugcccgccua auagggcguu augacuuguu      60
gaguucgaca ggaggcucac aacaggc                                         87

<210> SEQ ID NO 3
<211> LENGTH: 87
<212> TYPE: RNA
<213> ORGANISM: Artificial Sequence
<220> FEATURE:
<223> OTHER INFORMATION: Synthetic oligonucleotide

<400> SEQUENCE: 3
gggagacaag aauaaacgcu caaugcgcug aaugcccagc cgugaaagcg ucgauuucca     60
uccuucgaca ggaggcucac aacaggc                                         87

<210> SEQ ID NO 4
<211> LENGTH: 87
<212> TYPE: RNA
<213> ORGANISM: Artificial Sequence
<220> FEATURE:
<223> OTHER INFORMATION: Synthetic oligonucleotide

<400> SEQUENCE: 4
gggagacaag aauaaacgcu caaaugauug cccauucggu uaugcuugcg cuuccuaaag      60
agcuucgaca ggaggcucac aacaggc                                         87

<210> SEQ ID NO 5
<211> LENGTH: 87
<212> TYPE: RNA
<213> ORGANISM: Artificial Sequence
```

```
<220> FEATURE:
<223> OTHER INFORMATION: Synthetic oligonucleotide

<400> SEQUENCE: 5
gggagacaag aauaaacgcu caaggccaug uugaaugccc aacuaagcuu ugagcuuugg      60
agcuucgaca ggaggcucac aacaggc                                         87

<210> SEQ ID NO 6
<211> LENGTH: 71
<212> TYPE: RNA
<213> ORGANISM: Artificial Sequence
<220> FEATURE:
<223> OTHER INFORMATION: Synthetic oligonucleotide

<400> SEQUENCE: 6
gggagacaag aauaaacgcu caacaaugga gcguuaaacg ugagccauuc gacaggaggc      60
ucacaacagg c                                                          71

<210> SEQ ID NO 7
<211> LENGTH: 90
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (25)..(64)
<223> OTHER INFORMATION: n is a, c, g, or u

<400> SEQUENCE: 7
gggagagcgg aagcgugcug ggccnnnnnn nnnnnnnnnn nnnnnnnnnn nnnnnnnnnn      60
nnnncauaac ccagagguga uggaucccc                                       90

<210> SEQ ID NO 8
<211> LENGTH: 8
<212> TYPE: RNA
<213> ORGANISM: Artificial Sequence
<220> FEATURE:
<223> OTHER INFORMATION: Synthetic oligonucleotide

<400> SEQUENCE: 8 gaaugccc                                                               8
```